United States Patent
Shah

(10) Patent No.: US 10,984,913 B2
(45) Date of Patent: Apr. 20, 2021

(54) BLOCKCHAIN SYSTEM FOR NATURAL LANGUAGE PROCESSING

(71) Applicant: Netspective Communications LLC, Silver Spring, MD (US)

(72) Inventor: Shahid N. Shah, Silver Spring, MD (US)

(73) Assignee: Netspective Communications LLC, Silver Spring, MD (US)

( * ) Notice: Subject to any disclaimer, the term of this patent is extended or adjusted under 35 U.S.C. 154(b) by 861 days.

(21) Appl. No.: 15/389,243

(22) Filed: Dec. 22, 2016

(65) Prior Publication Data

US 2017/0103167 A1    Apr. 13, 2017

Related U.S. Application Data

(63) Continuation-in-part of application No. 13/457,782, filed on Apr. 27, 2012, now abandoned.

(51) Int. Cl.

| | |
|---|---|
| *G16H 50/20* | (2018.01) |
| *G06F 11/14* | (2006.01) |
| *G06F 16/951* | (2019.01) |
| *G06Q 10/10* | (2012.01) |
| *G16H 10/60* | (2018.01) |
| *G06F 40/40* | (2020.01) |
| *G06Q 50/00* | (2012.01) |

(52) U.S. Cl.
CPC ......... *G16H 50/20* (2018.01); *G06F 11/1464* (2013.01); *G06F 16/951* (2019.01); *G06F 40/40* (2020.01); *G06Q 10/101* (2013.01); *G16H 10/60* (2018.01); *G06F 2201/80* (2013.01); *G06F 2201/84* (2013.01); *G06Q 50/01* (2013.01)

(58) Field of Classification Search
CPC .... G06F 17/28; G06F 16/951; G06F 11/1464; G06F 2201/80; G06F 2201/84; G06F 40/40; G06F 50/01; G06Q 50/01; G16H 50/20; G16H 10/60
See application file for complete search history.

(56) References Cited

U.S. PATENT DOCUMENTS

| | | |
|---|---|---|
| 2002/0032583 A1 | 3/2002 | Joao |
| 2009/0164255 A1* | 6/2009 | Menschik .............. G16H 70/20 705/3 |

(Continued)

*Primary Examiner* — Fonya M Long
*Assistant Examiner* — Anthony Michael Balaj
(74) *Attorney, Agent, or Firm* — Rahman LLC

(57) ABSTRACT

A blockchain configured system includes a router and a blockchain configured record bank. The router collects data and converts it in a format in accordance with a defined standard. The blockchain configured record bank can include or be coupled to a data repository. The blockchain configured record bank can be configured to be coupled to the data provider through the router over a communication network. The blockchain configured record bank stores the data received from the data provider and can be accessible or searchable from within or outside the blockchain configured record bank. The blockchain configured record bank can be coupled to or include a data logging unit that maintains metadata associated with the data and configured to facilitate natural language processing capabilities. The router and the blockchain configured record bank may be coupled to machine learning system, metadata validation system, and master data validation system.

13 Claims, 10 Drawing Sheets

(56) References Cited

U.S. PATENT DOCUMENTS

| | | | | |
|---|---|---|---|---|
| 2010/0088286 A1* | 4/2010 | Bansode | ............... | G06F 16/83 |
| | | | | 707/667 |
| 2014/0046696 A1* | 2/2014 | Higgins | ............... | G16B 40/00 |
| | | | | 705/3 |
| 2014/0122126 A1* | 5/2014 | Riskin | ............... | G06F 16/35 |
| | | | | 705/3 |
| 2014/0368601 A1* | 12/2014 | deCharms | ............ | H04W 4/029 |
| | | | | 348/14.02 |
| 2015/0324535 A1* | 11/2015 | Ash | ............... | G16H 40/67 |
| | | | | 705/3 |
| 2015/0332283 A1* | 11/2015 | Witchey | ............... | H04W 12/02 |
| | | | | 705/3 |
| 2017/0149795 A1* | 5/2017 | Day, II | ............... | H04L 63/101 |
| 2018/0060496 A1* | 3/2018 | Bulleit | ............... | H04L 9/3239 |
| 2018/0129945 A1* | 5/2018 | Saxena | ............... | G06N 5/04 |
| 2018/0167200 A1* | 6/2018 | High | ............... | G16H 10/65 |

\* cited by examiner

BLOCKCHAIN SYSTEM FOR NATURAL LANGUAGE PROCESSING

CROSS-REFERENCE TO RELATED APPLICATIONS

This application is a continuation-in-part of U.S. patent application Ser. No. 13/457,782 filed on Apr. 27, 2012, the complete disclosure of which, in its entirety, is herein incorporated by reference.

BACKGROUND

Technical Field

The embodiments herein generally relate to blockchain systems, and more particularly, to blockchain systems used with natural language processing systems.

Description of the Related Art

Hospitals, caretakers, nursing centers or homes, medical offices, medical centers, or other sources of medical care generally keep medical and demographic or other such records of their patients. These records may include a variety of information such as demographic information of their patients, medical history, diagnostic and pathology reports of their patients, medical reports or prescriptions, or other such information. This information can be used for a variety of purposes by these sources of medical care. A few examples of them are, without limitations, tracking of the patients and their records, billing, historical assessments, future care taking, proper ongoing medical or health assessment or treatment, or any other similar purpose.

The medical sources may require collecting data from several sources to be stored in a central repository. The data obtained from these varied sources may exist in different digital formats and may not be standardized in accordance with a defined format. This may cause difficulty in handling of the data by the medical sources resulting in mismanagement, data leakage, data loss, data asynchronization, or any other such loss.

Additionally, searching the data or a specific portion of the data may be difficult in cases where the data exists in a non-standardized manner. Particularly, searching for the data from within the metadata may be extremely difficult from within the medical source or from outside.

In light of the above, there is a need of a system configured to retrieve data from varied medical sources and convert it in a standardized digital format before storing into a data bank of a medical source. There is also a need of a system configured to provide a natural language capability operable on the metadata and master data and allowing indexing and searching from within the medical source or from outside possible and easy and also provide appliances to syndicate the standardized data at distributed locations physically.

SUMMARY

An embodiment herein provides a blockchain configured geographically distributed architecture-based system connected over a communication network for transforming unstructured or semi-structured dataset to structured computerized dataset for a blockchain configured records database communicatively coupled to a plurality of blockchain configured content based routers receiving the unstructured or semi-structured dataset from a plurality of data provider computers in a blockchain-enabled network. The system includes a first proxy database, stored on a first tangible non-transitory computer readable medium and comprising a first special purpose processing device implemented on a first integrated circuit chip. The first proxy device is configured to create a backup of data associated with a first data provider computer, wherein the data associated with the first data provider computer is in a first digital format. The first proxy device is configured to communicate with the first data provider computer for backing up the data associated with the first data provider computer, through a first proxy object, wherein the first proxy object comprises one or more references to the first proxy database to establish a connection between the first data provider computer and the first proxy database through one or more database drivers. The system includes a blockchain configured first content based router of the plurality of blockchain configured content based routers, comprising a second special purpose processing device implemented on a second integrated circuit chip, configured to collect the data associated with the first data provider computer from the first proxy database and convert the data associated with the first data provider computer to the structured computerized dataset in accordance with a standardized digital format of dataset associated with the blockchain configured records database. The blockchain configured first content based router is physically located at a gateway associated with the first data provider computer providing a first digital data access point of the distributed blockchain configured records database to the first data provider computer. The system includes the blockchain configured records database stored on a third tangible non-transitory computer readable medium and including a fifth special purpose processing device implemented on a fifth integrated circuit chip to store and index the structured computerized dataset in the standardized digital format, and providing a plurality of distributed digital data access points including the first digital data access point communicatively connecting with the first data provider computer through the distributed first digital data access point of the plurality of distributed digital data access points. The system includes a master data validation system communicatively and operatively coupled to the blockchain configured first content based router and the blockchain configured records database and including a master data repository to store master data instances in the standardized digital format on a tangible non-transitory memory device. The system includes a metadata validation system different and separately located from the master data validation system and communicatively and operatively coupled to the blockchain configured first content based router, the blockchain configured records database and the master data validation system, and configured to store linkable metadata layer objects in a metadata layer repository and digitally link the metadata layer objects by storing an identifier to a source content residing in the blockchain configured records database. The blockchain configured first content based router is connected to a machine learning system communicatively coupled with the blockchain configured records database. The machine learning system includes internal extensible taxonomies built in a computerized format based on the structured computerized dataset in the blockchain configured records database. The internal extensible taxonomies are defined through a computerized category profile wherein the computerized category profile includes digitally stored parent terms and digitally stored child terms and associated digital identifiers indicative of the respective digitally stored parent terms, digitally stored child terms and pointers indicating mutual connections in a hierarchical pattern. The machine learning system includes external taxonomies pulled from external systems not connected with the blockchain configured records database directly and crawled by accessing the external systems with the use of a search engine-enabled crawler to merge with the internal extensible taxonomies digitally by mapping comparable terms in the external taxonomies with the category profile of the internal extensible taxonomies. The machine learning system includes a memory circuit to store the internal extensible taxonomies and the external taxonomies that are digitally merged with the internal extensible taxonomies. The machine leaning system includes a semantics learning appliance comprising a seventh special purpose processing device implemented on a seventh integrated circuit chip configured to perform mapping of the inflowing unstructured or semi-structured dataset with the structured computerized dataset already stored in the blockchain configured records database and the master data and the metadata. A dedicated first local machine housed in a material frame is operatively and communicatively coupled to the first data provider computer and installed physically behind a firewall and communicatively connected with the remotely located blockchain configured records database to transmit said structured computerized dataset at least in part from said blockchain configured records database to said first data provider computer through a digital transmission channel based on access rights and upon identity verification of the first local machine by the blockchain configured records database.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION

Figure 1:
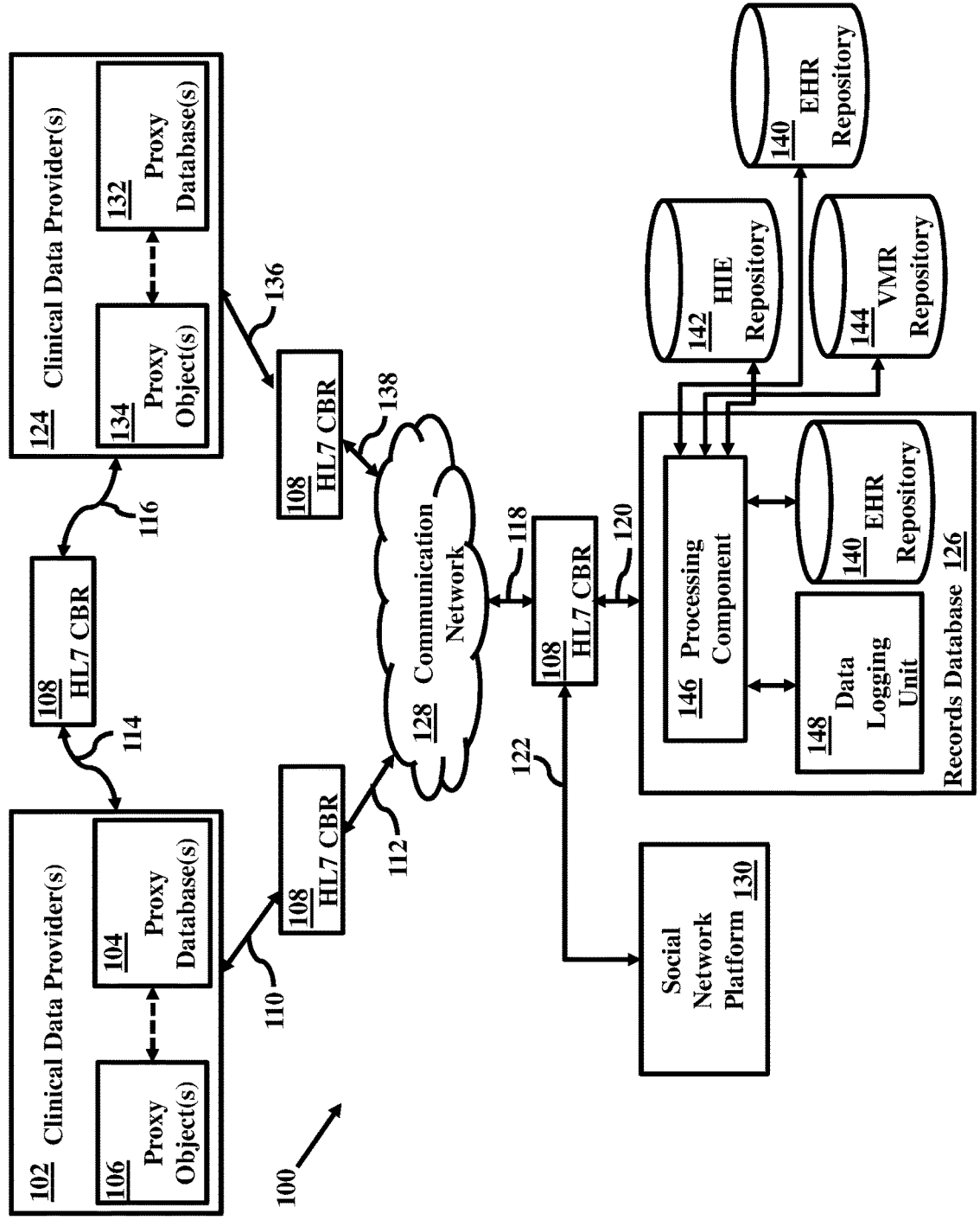
FIG. 1 is a schematic diagram illustrating a high level system architecture according to an embodiment herein.

The embodiments herein and the various features and advantageous details thereof are explained more fully with reference to the non-limiting embodiments that are illustrated in the accompanying drawings and detailed in the following description. Descriptions of well-known components and are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

In the following detailed description, reference is made to the accompanying drawings that form a part hereof, and these are shown by way of illustrating specific embodiments herein that may be practiced. These embodiments, which are also referred to herein as "examples," are described in sufficient detail to enable those skilled in the art to practice the embodiments herein, and it is to be understood that the embodiments may be combined, or that other embodiments may be utilized and that structural, logical, and electrical changes may be made without departing from the scope of the embodiments herein.

In this document, the terms "a" or "an" are used, as is common in patent documents, to include one or more than one. In this document, the term "or" is used to refer to a "nonexclusive or" unless otherwise indicated.

In an exemplary embodiment, the various modules described herein and illustrated in the figures are embodied as hardware-enabled modules and may be configured as a plurality of overlapping or independent electronic circuits, devices, and discrete elements packaged onto a circuit board to provide data and signal processing functionality within a computer. An example might be a comparator, inverter, or flip-flop, which could include a plurality of transistors and other supporting devices and circuit elements. The modules that are configured with electronic circuits process computer logic instructions capable of providing digital and/or analog signals for performing various functions as described herein. The various functions can further be embodied and physically saved as any of data structures, data paths, data objects, data object models, object files, database components. For example, the data objects could be configured as a digital packet of structured data. The data structures could be configured as any of an array, tuple, snap, union, variant, set, graph, tree, node, and an object, which may be stored and retrieved by computer memory and may be managed by processors, compilers, and other computer hardware components. The data paths can be configured as part f a computer CPU that performs operations and calculations as instructed by the computer logic instructions instructions. The data paths could include digital electronic circuits, multipliers, registers, and buses capable of performing data processing operations and arithmetic operations (e.g., Add, Subtract, etc.), bitwise logical operations (AND, OR, XOR, etc.), bit shift operations (e.g., arithmetic, logical, rotate, etc.), complex operations (e.g., using single clock calculations, sequential calculations, iterative calculations, etc.). The data objects may be configured as physical locations in computer memory and can be a variable, a data structure, or a function. In the embodiments configured as relational databases (e.g., such Oracle® relational databases), the data objects can be configured as a table or column. Other configurations include specialized objects, distributed objects, object oriented programming objects, and semantic web objects, for example. The data object models can be configured as an application programming interface for creating HyperText Markup Language (HTML) and Extensible Markup Language (XML) electronic documents. The models can be further configured as any of a tree, graph, container, list, map, queue, set, stack, and variations thereof. The data object files are created by compilers and assemblers and contain generated binary code and data for a source file. The database components can include airy of tables, indexes, views, stored procedures, and triggers.

The embodiments herein provide a system and method of transformation of unstructured and semi-structured data into structured data by creating metadata and master data-based natural language processing capabilities involving machine learning tools and systems. Referring now to the drawings, and more particularly to FIGS. 1 through 4, where similar reference characters denote corresponding features consistently throughout the figures, there are shown preferred embodiments.

FIG. 1 illustrates generally, but not by the way of limitation, among other things, an example of a high level system architecture 100 according to an embodiment herein. The architecture 100 can include a records database 126 to store health records coming from a variety of sources such as from a plurality of clinical data providers through an HLR Content Based Router (CBR) 108. The records database is also configured to manage metadata and master data information associated with the health records. The records database 126 can be configured to create natural language data processing capabilities in accordance with the defined metadata and master data information over a communication network 128.

In particular, as shown in FIG. 1, a plurality of clinical data providers 102, 124 and a social network platform 130 can be sources of health records. The clinical data provider 102 for example can be a hospital, a clinic, a medical organization, a physician's office, etc. As shown in FIG. 1, the clinical data provider 102 can include internal systems (which can, for example, include database or possess data storage capabilities). The clinical data provider 102 can be configured to interact with a proxy database 104 to backup the data related to the clinical data provider 102. The clinical data provider 102 can backup the data on the proxy database 104 through the one or more proxy objects 106. The one or more proxy objects 106 may include references to the proxy database 104 to establish a connection between the clinical data provider 102 and the proxy database 104 through the database drivers. These database drivers are explained in more detail in conjunction with FIG. 2. The data described herein can be for example, but is not limited to, doctor's visits, lab tests, hospital stays, clinical trials, patient problems, patient health information, patient habits, patient medical history, patient appointments, patient medical insurance, patient medical bills and related status, or any other data.

A Health Level 7 (HL7) Content Based Router (CBR) 108 configured as a hardware appliance can be employed that is associated with a database or data storage facility or capability, and can include a local internal interface to handle direct links such as 110, 112, 114, 116, 118, 120, or 122 to communicate with other nodes such as the clinical data providers 102, and 124, and the records database 126 over the communication network 128. In an example, the HL7 CBR 108 can be situated at a gateway of the sources of health records such as the clinical data providers 102, 124, the network platform 130; and/or the records database 126 to communicate among each other over the communication network 128. In some embodiments, several HL7 CBRs similar to the HL7 CBR 108 can be situated at more than one or each of the gateways. For example, three such HL7 CBRs 108 are shown in the FIG. 1. In an example, a respective HL7 CBR 108 can be configured to be situated at the clinical data providers 102, 124 endpoints, the network platform 130 endpoints, or the records database 126 endpoints to communicate amongst each other over the communication network 128. In some embodiments, only one common HL7 CBR 108 may be configured at the endpoint or gateway of the records database 126, such that the records database 126 can exchange, integrate, share, receive or provide data to or from the nodes such as the one or more clinical data providers 102, 124, or the social network platform 130, or any other node. The CBR 108 may be managed, operated, and controlled by the records database 126, in an embodiment, and may be located proximate the records database 126 and remote from the clinical data providers 102, 124, 130. The HL7 CBR 108 can be configured to collect data from the one or more proxy databases such as the proxy database 104 and 132. The HL7 CBR 108 can be configured to convert the data in a common digital format such as in accordance with the HL7 standard such that the data within the communication network 128 between the HL7 CBR 108 may comply with the common digital format and is validated according to a single standard or mechanism such as the HL7 standard. The HL7 standard described herein may provide a framework for the exchange, integration, sharing, or retrieval of health information from or to the records database 126. In an example, the HL7 standard can also be used to refer to some of the specific standards such as HL7 v2.x, v3.0, HL7 Reference Information Model (RIM), etc. created by the organization such as the clinical data providers 102 and 124, the social network platform 130, or the records database 126.

In an example, the clinical data provider 102 may interact with other clinical data provider 124 through the HL7 CBR 108 via the records database 126 or without records database 126 to exchange data amongst each other. The clinical data provider 124 described herein can be configured to include a proxy database 132 to backup clinical data associated with the clinical data provider 124. The clinical data provider 124 can be configured to include one or more proxy objects 134 to backup data on the proxy database 132. The one or more proxy objects 134 described herein may include references to the proxy database 132 to establish a connection among the clinical data provider 124 and the proxy database 132 through the database drivers. The proxy database 132 can be configured to interact with the HL7 CBR 108 through the direct links such as 114, 116, 118, 120, 122, 136, or 138 to communicate with other nodes such as other content service providers 102, and the records database 126 over the communication network 128.

The communication network 128 described herein can be configured to provide a communicative interconnection of various nodes such as the clinical data providers 102, 124, the records database 126, the social network platform 130, or any other node in the communication network 128. The communication network 128 can be configured to facilitate the various nodes to exchange, integrate, share, receive or provide data among each other, in accordance with the HL7 standard facilitated by the respective HL7 CBR 108 (may be configured at the endpoint or at the gateway of the organization). The communication network 128 may be a wireless communications network or a wire line communications network. The wireless communications network may be for example, but not limited to, a digital cellular network, such as Global System for Mobile Telecommunications (GSM) network, Personal Communication System (PCS) network, or any other wireless communications network. The wire line communications network may be for example, but not limited to, a Public Switched Telephone Network (PSTN), proprietary local and long distance communications network, or any other wire line communications network. One or more networks may be included in the communication network 128 and may include both public networks such as the Internet, and private networks and may utilize any networking technology and protocol, such as Ethernet, Token Ring, Transmission Control Protocol/Internet Protocol (TCP/IP), or the like to allow interaction among various nodes such as the clinical data providers 102, 124, the records database 126, the social network platform 130, or any other node in the network. In an embodiment, the social networking platform 130 may generate a variety of data coming from various aggregators and user profiles comprising of a plurality of digital formats wherein each digital format may be associated with a specific structure different from other digital formats. The data originating from the social networking platform 130 may require complex mapping of fields and elements for transformation to a unified structure as per records database 126 requirements. The social networking platform 130 may host information related to one or more clinical data providers of the type of 104 and 124. For example, the social networking platform may host social profiles of the clinical data providers where they may store and update their personal, professional or other such details or may communicate in a social network with friends, relatives, family members, or other such networking contacts about healthcare information or patient or medical device generated information, in an example. The social networking platform 130 may be defined as a network with an arbitrary large number of networked computers accessing the social network 130 through registered social profiles of such as clinical data providers. The social networking platform 130 may facilitate posting and sharing online profiles, data, clinical reviews, patient generated data, device generated data, IoT data, sensors data etc, simultaneously viewable by each of the arbitrary large number of computers including such as a clinical provider computer, reviewer's computer, third party's computer, patient's computer, and the like.

In an example, where a single and common HL7 CBR 108 may be provided at the gateway of the records database 126, the communication network 128 may be configured to translate or convert the data at the common HL7 CBR 108 to exchange, integrate, share, receive, or provide data to or from the various nodes connected with the communication network 128 using various machine learning, metadata and master data validation systems as will be discussed later in the document. The common HL7 CBR 108 may comply with the common digital data format and may be validated according to the single standard or mechanism such as the HL7 standard, for example when information first enters the records database 126.

The records database 126, described herein, may be centralized or decentralized or may be blockchain configured to allow access of the records database 126 through a distributed blockchain configured network as discussed later in conjunction with FIG. 9. In embodiments, the records database 126, and various content based routers 108 may be blockchain configured. The blockchain configured records database 126 and associated components, also referred to as a "smart contract based distributed integrity network", may not require a centralized health information exchange (HIE) operator because all participants may have access to distributed ledgers to maintain a secure exchange without broken trusts. This allows disintermediation by removing human participants from a chain of the participants such as the clinical data providers 102 and 124 and networks 130. Additionally, the health records are distributed across a plurality of storage locations in the blockchain accessible by the participants simultaneously and allowing to make updates almost in real time. The blockchain configured ecosystem provides a secured, disintermediated and distributed framework to amplify and support integration of healthcare information across a range of uses and stakeholders defined by the entities. The blockchain configured digital ecosystem, also referred to as a smart contract based distributed integrity network, facilitates a secured and distributed framework for patient digital identities to allow access to body worn personally connected health devices, connected health devices at home and other facilities, storage devices and servers hosting the medical records and the like, with the use of private and public keys secured through cryptography and thus protecting identity by allowing a restricted access to a particular clinical provider in accordance with dynamic rules and policies along with strong identity validation mechanisms using blockchain configured validation devices across the integrity network. The distributed nature of the blockchain configured digital ecosystem enables shared data which provides near real-time updates across a network accessible to all authorized entities without the need for a centralized authority or exchange.

The records database 126 may store the data provided by the plurality of clinical data providers and associated computers and networks in an electronic healthcare (EHR) repository 140, a Health Information Exchange (HIE) repository 142, a Virtual Medical Records (VMR) repository 144, etc. to store, exchange, integrate, share, receive, or provide data through the HL7 CBR 108. The EHR repository 140 can for example store the data such as electronic healthcare records. The data can be organized in a way that facilitates local or remote access and retrieval and indexing in the communication network 128 through a processing component 146. In some embodiments, the processing component 146 may be, but is not limited to, a microprocessor, a microcontroller, or the equivalent. The processing component 146 may be capable of executing instructions to process data over the communications network 128. The data corresponding to a particular user may or may not have been derived from medical testing or treatment (e.g., the data may have been derived from a research organization trial in which an individual voluntarily participated or data may have been derived from insurance services or any other source).

More generally, the records database 126 may also include data related to different electronic sources such as doctor's visits, lab tests, hospital stays, clinical trials, patient problems, patients' health information, patient habits, patient medical history, patient appointments, patient medical insurance, patient medical bills status, or any other information. The records database 126 may include or be coupled to other electronic data stores such as the HIE repository 142 and the VMR repository 144 to dynamically manage information related to or from the electronic sources. The HIE repository 142 may include electronic healthcare information related to a region, community, or hospital system. In examples, the HIE repository 142 may provide additional storage, retrieval, and manipulation of information such that the records database 126 can dynamically mange EHR data through the HL7 CBR 108. The VMR repository 144 described herein may store data related to the electronic medical information or other sources. The virtual medical records, described herein, may be a simplified, standardized electronic health record data designed to support interfacing to the records database 126. The records database 126 may include or be coupled to a data logging unit 148. The data logging unit 148 can be configured to receive the data from the proxy databases 106 and 134 through the HL7 CBR 108. The HL7 CBR 108 can be configured to translate or convert the data moving to or coming from the proxy database such as 106 or 134. Natural Language Processing (NLP) capabilities can be created, in accordance with metadata learned from the database drivers. Additional details about the data logging unit 148 are provided in conjunction with FIG. 2 and described below. The data logging unit 148, in an embodiment, may include various machine learning, master data and metadata validation systems that may facilitate transformation and standardization of unstructured or semi-structured data (also referred to as dataset interchangeably) coming from the clinical data providers and networks 124, 104, and 130. In an embodiment, multiple data logging units similar to the data logging unit 148 may be integrated within each of the CBR 108 so that each CBR 108 can perform entire standardization, transformation, and data logging tasks using various machine learning, metadata validation and master data validation systems. In an embodiment, a single data logging unit similar to the data logging unit 148 may be deployed and integrated or coupled with the records database 126 and operatively and/or communicatively coupled to the CBR 108 so as the CBR 108 to utilize inputs from the records database 126 and the associated data logging unit 148 to perform transformation and standardization tasks.

The description provided above includes proxy objects such as 106 and 134, and proxy databases such as 104 and 132, in accordance with some examples, however, it should be appreciated that there can be other techniques used by those skilled in the art that can be embodied without using proxy objects and the proxy databases.

Figure 2:
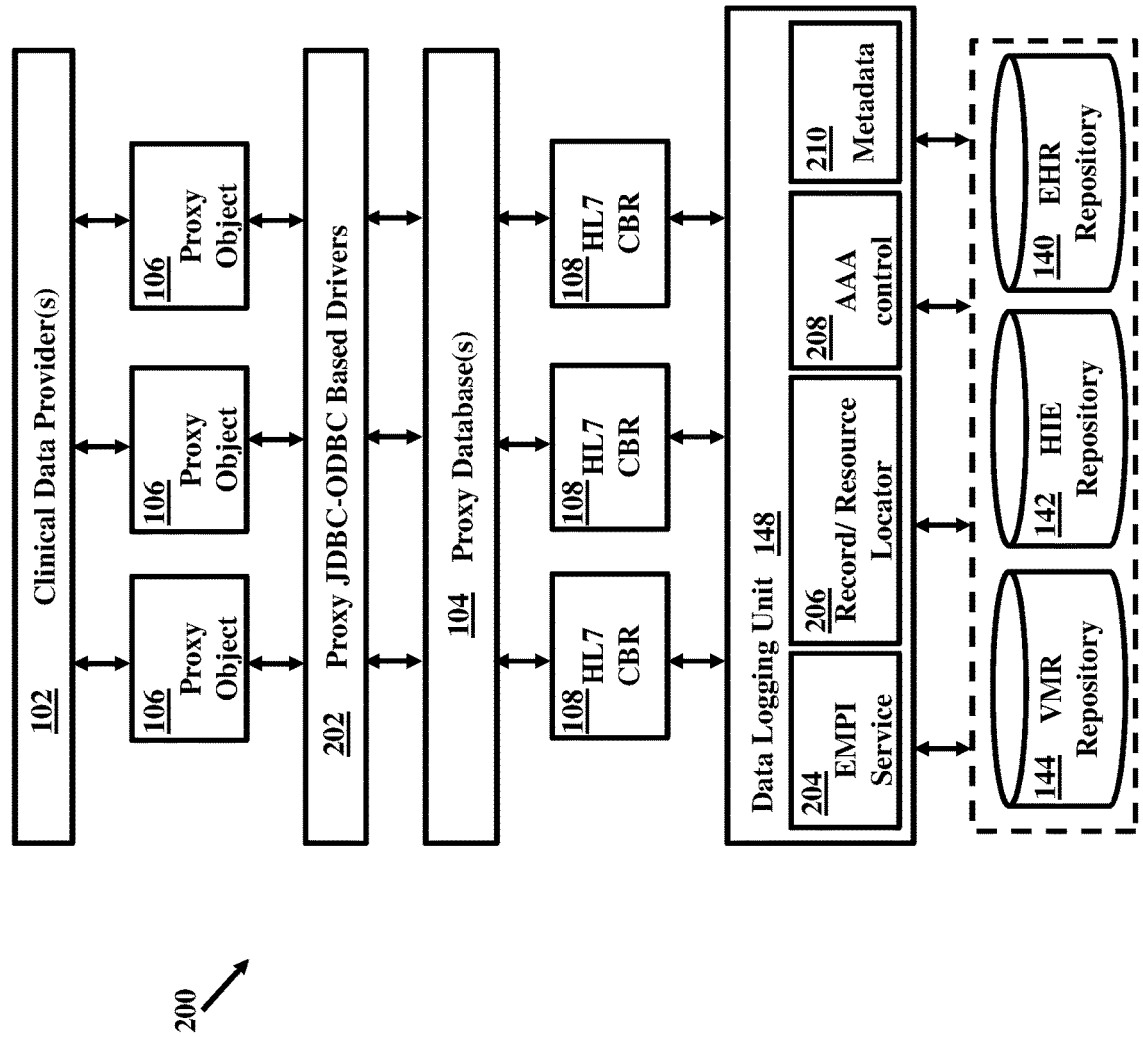
FIG. 2 is a schematic diagram illustrating a functional overview of the system architecture of FIG. 1 according to an embodiment herein.

FIG. 2, with reference to FIG. 1, illustrates generally, but not by the way of limitation, among other things, a functional overview of the system 200 as described in FIG. 1, in accordance with the embodiments herein. The clinical data provider 102 can be configured to backup data on the proxy database 104. The clinical data provider 102 can be configured to connect to the proxy database 104 to backup the data on the proxy database 104. In an example, the clinical data provider 102 may not directly connect to the proxy database 104 to avoid security problems. Therefore, the clinical data provider 102 can be configured to use the one or more proxy objects 106 to connect to the proxy database 104.

The clinical data provider 102 can be configured to establish a connection to communicate with the proxy database 104. The clinical data provider 102 may implement a common set of routines (such as classes) to connect to the proxy database 104 through proxy JDBC-ODBC drivers (Java Database Connectivity and Open Database Connectivity Drivers) 202. The JDBC-ODBC database drivers 202 described herein are only for illustrative purposes, and the embodiments herein are not limited to these types of drivers. In some embodiments, there may be other database drivers such as MySQL®, Oracle®, or any other database driver to connect to the proxy database 104. In some examples, other drivers or interfaces such as database interfaces or frameworks may also be employed. The connection with the proxy database 104 may be established by loading a class of appropriate proxy JDBC-ODBC drivers 202. The system 200 can be configured to allow the clinical data provider 104 to create the one or more proxy objects 106 whose functions can be mirrored with the functions of the proxy Java Database Connectivity (JDBC) objects created on the proxy database 104. The clinical data provider 102 may then use these proxy objects 106 to communicate with the proxy database 104. This may result in creating a session on the clinical data provider 102 for each call to a DriverManager. connect( ) object. This object may be the proxy for the actual session object on the proxy database 104, used later to execute methods to backup data and create statements on the proxy database 104. An example using such proxy JDBC-ODBC Driver 202 is shown in the code below:

```
// creates a connection object on the proxy databaseConnection
con=JDBCDriver.connect("jdbc:odbc:Database");//
Load the proxy database drivers
    Class.forName( "sun.jdbc.odbc.JdbcOdbcDriver") ;
    // Get a connection to the proxy database through the proxy database
    drivers
    Connection con = DriverManager.getConnection(
        "jdbc:odbc:Database");
```

In an example, a batch of data may be sent through the clinical data provider 102 to backup on the proxy database 104. The call to the proxy database 104 by the clinical data provider 102 may be batched for better performance. The batch of statements (such as including queries to backup the data on the proxy database 104) may be sent to the proxy database 104. The proxy database 104 may execute the batch of statements in sequence, parallel, or a combination thereof. In an example, the proxy database 104 may return a result set such as a unique name of the proxy object 102 (e.g., Connection, Statement, Prepared Statement etc.) created on the proxy database 104. In an example, the proxy database 104 may execute the batch of statements and return the result set such as a null object. In an example, one or more exceptions thrown by the proxy database 104 may be serialized and may be sent to the clinical data provider 102 (if exceptions occur). If the execution of the statements results in creating one or more new proxy objects on the proxy database 104, then the unique name of the one or more proxy objects is returned to the clinical data provider 102 (for use to later connect and backup the data). In an example, the clinical data provider 102 may override the finalize( ) method, such as the proxy object 106 may be garbage collected (by the use of finalize( ) method) on the clinical data provider 102. In an example, the actual proxy objects 102 may also be removed from the proxy database 104 and may also be garbage collected (upon overriding the finalize( ) method). An example using such batch processing is shown below as a piece of code.

```
// creates a Connection object on the proxy database
Connection connection=JDBCDriver.connect("jdbc:odbc:Database");
// -start batch
PreparedStatementps=connection.PrepareStatement(String);
ps.setString(1, String);
ps.setInt(2, int);
ps.setDate(3, Date);
ResultSetrset=(ResultSet)ps.executeQuery( );
//- end batch
```

The proxy database 104 may then interact with the respective HL7 CBR 108 to convert or translate the data into a common digital format such as the HL7 standard and provide the converted or translated data to the records database 126. In an example, the HL7 CBR 108 may be configured to implement data correlation technology such that the data can be integrated into a common format.

The records database 126 and/or the CBR 108 can be configured to include the data logging unit 148. The data logging unit 148 can be configured to track a unique network identifier associated with the HL7 CBR 108 such that the data or piece of information received from the respective HL7 CBR 108 can be uniquely identified through a local identifier associated with the data. The data logging unit 148 can be configured to maintain an Enterprise Master Patient Index (EMPI) service 204, a Record or Resource Locater Service 206, an AAA (Authentication, Authorization, Accounting) 208 or security technologies (for e.g., to store or track current or past data or authorizations provided by, or on behalf of, or relating to different clinical data providers), a metadata and/or master data validation service 210 to facilitate the NLP capabilities such as for example the metadata and master data learned from the proxy database drivers 202.

The EMPI service 204 can be configured to manage the patient's identifier from the respective HL7 CBR 108, EHR repository 142, HIE repository 144, or VMR repository 144 to help it identify and locate appropriate records data. The information about the EMPI 204 is configured to define, use, interpret, and normalize the master data and metadata 210 across the system 200. In an example, a common metadata and master data configuration can be maintained by the data logging unit 148 or associated systems for the data received from the respective HL7 CBR 108. Further, the data logging unit 148 can be configured to maintain a common way to represent the HL7 CBR 108 data (from a plurality of proxy databases similar to the proxy database 102 and 124) in a metadata and master data store. Each of the HL7 CBRs 108 in the communication network 128 can be configured to describe certain information to define metadata, which can be configured during deployment of the HL7 CBR 108. In an example, the data logging unit 148 can be configured to populate the metadata store in accordance with each HL7 CBR identifier such as name, ID, or any other mechanism that can uniquely identify the data provided by each HL7 CBR 108. In an example, the data logging unit 148 can be configured to maintain the metadata configuration in accordance with the HL7 CBR identifier.

An example of such metadata can be Title: metadata HL7 CBR, Identifier: govhealthcare.com, format: HL7 Standard, provider: clinical data provider, connection:
  proxy database drivers.

The data logging unit 148 can be configured to facilitate an XML search structure to provide NLP capabilities over the communication network 128. In an example, the data logging unit 148 may be configured to define the metadata using the Get( ) method from the HL7 CBR 108 and provide the data to the HL7 CBR 108 using the Put( ) method. In an example, the metadata is defined from the proxy database drivers 202 such as shown in the code below:

```
classJDBCProxyDatabaseMetaDataExample
// Createa connection object on the proxy database
Connection con=JDBCDriver.connect("jdbc:odbc:Database");
// Load the proxy database drivers
Class.forName( "sun.jdbc.odbc.JdbcOdbcDriver" ) ;
// Get a connection to the proxy database through the proxy database
drivers
Connection con = DriverManager.getConnection( "jdbc:odbc:Database")
//Metadata configuration data retrieval from the proxy database drivers
DatabaseMetaDatametaData = con.getMetaData( )
ResultSetrs = metaData.getTypeInfo( );
//Query statements for metadata information from the proxy database
drivers
ResultSetresultSet = st.executeQuery("SELECT * FROM
proxydatabase");
ResultSetMetaData md = resultSet.getMetaData( );
```

In an example, the data logging unit 148 can be configured to deploy the metadata configuration as a separate schema into either a directly attached records database 126 or shared data repositories such as the HIE repository 142 or the VMR repository 144 supported by an overall records database 126 deployment. The records database 126 can be configured to provide NLP capabilities, in accordance with the defined metadata configuration and master data configuration learnt from the proxy database drivers 202 and the respective HL7 CBR 108 and master data systems.

In an example, the system 200 as described above can be configured to support various languages such that the system 200 can be configured to search for data and extract information or the data irrespective of the language of the metadata contained therein. In an example, the system 200 can be configured to check for security such as monitoring for data leakage.

In an example, the data logging unit 148 may include or be coupled to various machine learning, master data, and metadata validation systems. In an example, the data logging unit 148 may be integrated or coupled with the records database 126 or may be integrated or coupled with the CBR 108. In accordance with these embodiments, the metadata and master data validation tasks, NLP functions, and machine learning can be performed by either the records database 126 and its associated systems or by the CBR 108.

Figure 3:
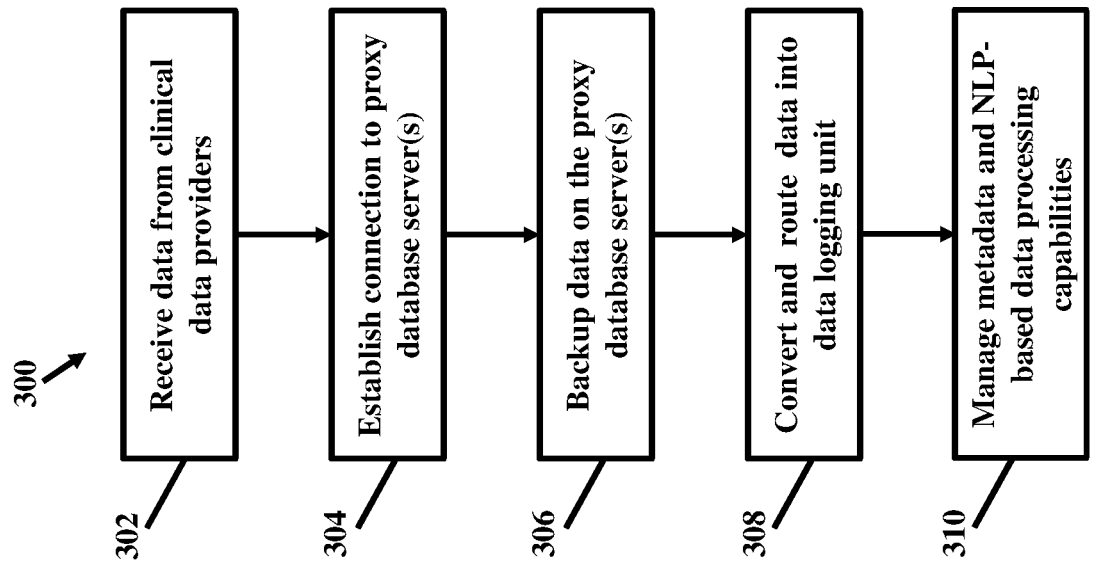
FIG. 3 is a flow chart illustrating a method of creating natural language based data processing capabilities from metadata facilitated by proxy database drivers according to an embodiment herein.

FIG. 3, with reference to FIGS. 1 and 2, illustrates generally, but not by the way of limitation, a flow chart depicting a method 300 for creating natural language based data processing capabilities from metadata facilitated by the proxy database drivers 202 and master data, according to an embodiment herein. At step 302, the method 300 may include receiving data from clinical data providers such as the clinical data provider 102. At step 304, the clinical data provider 102 can establish a connection with the proxy database 104 using the proxy database drivers 202. At step 306, the clinical data provider 102 may backup the data on the proxy database 104. At step 308, the method 300 may allow the HL7 CBR 108 to convert or translate the data into a common digital format such as HL7 standard using various machine learning, metadata, and master data validation systems. In an embodiment, the method 300 may allow the HL7 CBR 108 to route the data into the data logging unit 148. In an embodiment, the logging unit and various machine learning, metadata, and master data validation systems may be integrated within or coupled to the CBR 108.

At step 310, the data logging unit 148 or the CBR 108 and associated machine learning, metadata, and master data validation systems can manage the metadata learnt from the proxy database drivers 202 such that the records database 126 and/or the CBR 108 creates NLP-based data processing capabilities, in accordance with the defined metadata configurations. In certain embodiments, the data logging unit 148 and/or the CBR 108 may include the machine learning system, the master data validation system, and the metadata validation system as will be discussed later in conjunction with various figures.

Figure 4:
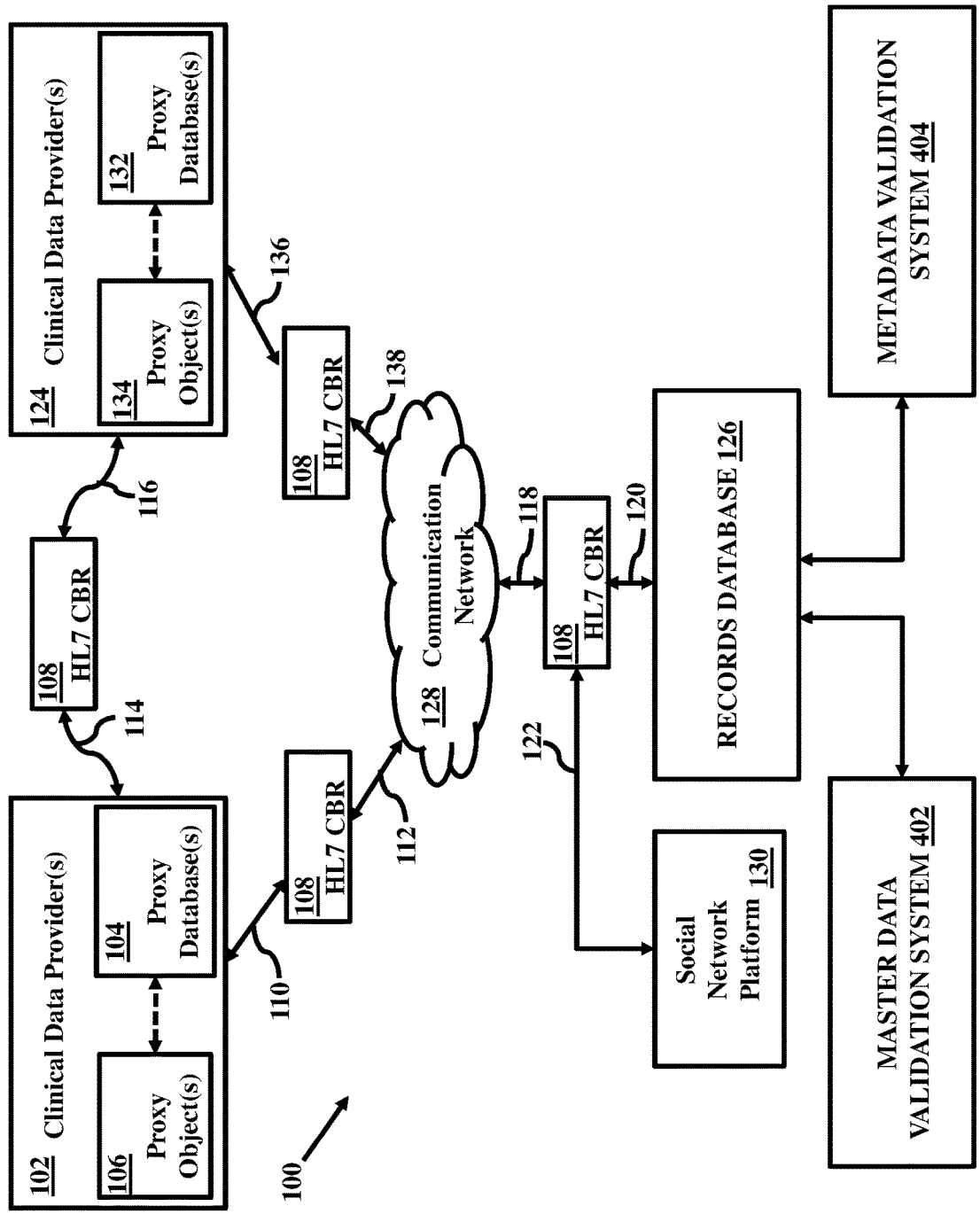
FIG. 4 is schematic diagram illustrating a high level system architecture with a record bank communicatively coupled to a master data validation system and a metadata validation system according to an embodiment herein.
Figure 5:
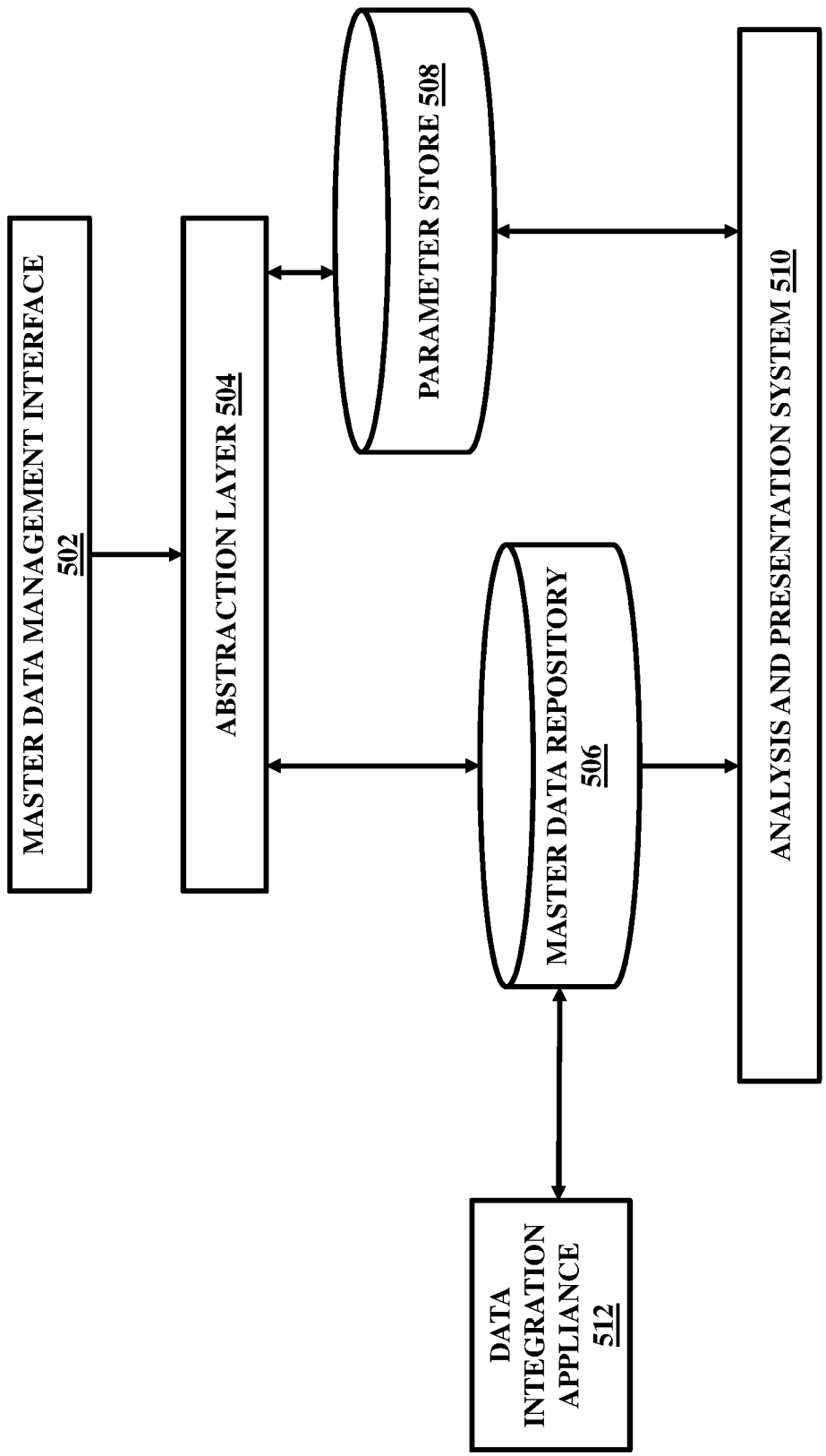
FIG. 5 illustrates a detailed architecture diagram of the master data validation system according to an embodiment herein.
Figure 6:
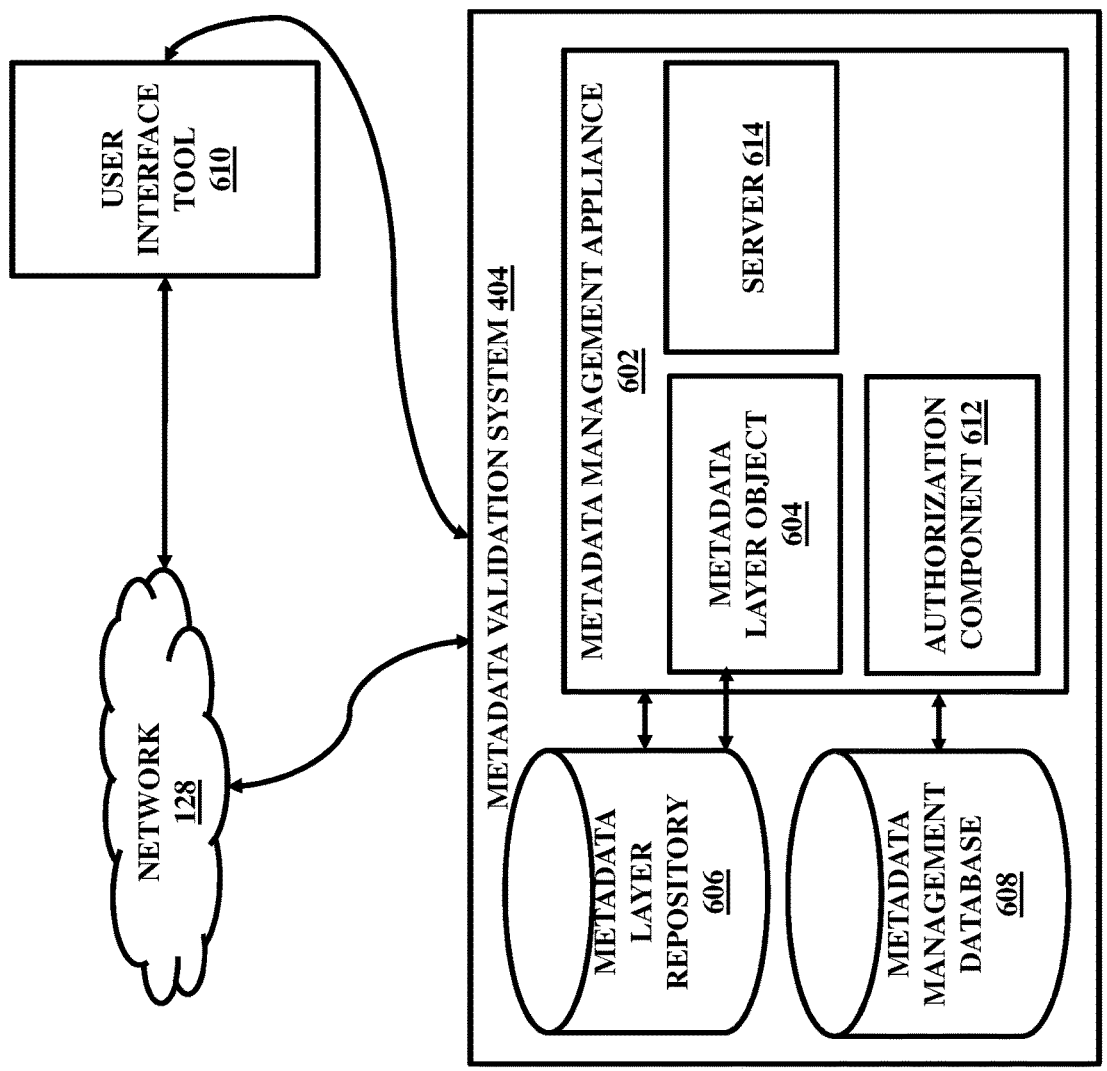
FIG. 6 illustrates a detailed architecture diagram of the metadata validation system according to an embodiment herein.

As shown in FIG. 4, the records database 126 and/or the CBR 108 may be connected with a separately located master data validation system 402 and a metadata validation system 404 that respectively store master data and metadata for improving natural language processing using machine learning tools over time with the use of the data logging unit 148 and the processing component 146. In an embodiment, the processing component 146 may be included within the data logging unit 148. In an embodiment, the processing component 146 may be separately located and communicatively and operatively coupled to the data logging unit 148 for processing various functions. FIG. 5 illustrates a detailed architecture diagram of the master data validation system 402. FIG. 6 illustrates a detailed architecture diagram of the metadata validation system 404.

The master data validation system 402 may facilitate in creating a unified view of entire health data stored in or associated with the records database 126 and entire enterprise data generated through multiple sources. The master data validation system 402 can uniquely identify each instance of a business element such as source name, source location, patient or healthcare entity's names and locations, enterprise product names, accounts, etc and represent these instances using a standardized data model. The master data validation system 402 allows to create a single source of truth around which enterprise systems including the records database 126 can be synchronized. The master data validation system 402 extracts key data from diverse operational environments to create a system of record files and establish links to keep the system 404 and operational system files synchronized, and providing fast access across all operational systems to the master data without degrading operational performance. The master data validation system 402 is configured to harmonize, store and maintain master data over time through use of hardware and software elements to increase consistency and accuracy of healthcare performance reporting by enabling participants to collaboratively control and maintain master data in a workflow-driven web-based environment. The master data validation system 402 provides a consistent context against which healthcare performance can be measured. The master data validation system 402 may include a master data validation interface 502, an abstraction layer 504, a master data repository 506, a parameter store 508, an analysis and reporting system 510, and a data integration appliance 512.

The data integration appliance 512 includes elements for data integration, data syndication and workflow execution. The data integration appliance 512, for example may be a specialized engine including specialized hardware and software components for data extraction, transformation and ingestion. The data integration appliance 512 is responsible for transporting master data. The management interface 502 may be a role-based user interface that may allow appropriate functionality for data visualization and data management to users and application administrators. The abstraction layer 504 is an application programming interface (API) that enables other systems to access and manipulate master data in a well-defined way. The parameter store 508 may assist in providing an adaptive extensible framework for unified master data across the entire health data repositories. The parameter store 508 may store control information that specifies behavior of master data validation processes and data representation using a set of predefined rules and guidelines.

The master data repository 506 may store entire master data information in a standardized format. The master data repository 506 may interact with the analysis and presentation system 510 which selectively provides master data reports, data quality reports, and allow display and presentation of requested master data information by pulling it from the master data repository 506.

Referring to FIGS. 4 and 6, the metadata validation system 404 is discussed herein, in an embodiment. The metadata validation system 404 is configured to create and organize a new metadata layer object instance upon recognition of an event or a trigger indicative of a new metadata layer object 604. The metadata validation system 404 includes a metadata validation appliance 602, a metadata layer repository 606, and a metadata validation database 608.

The metadata validation system 404 may provide a user interface tool 610 to allow a user or an administrator to access and/or view and/or extract a portion of the content stored in the metadata layer repository 606. The metadata layer repository 606 is configured to store linkable metadata layer objects 604. Once a metadata layer object 606 is created or updated, the metadata validation system 404 is configured to store the created metadata layer object 604 in the metadata layer repository 606. In an embodiment, the metadata layer repository 606 can be associated locally to each of the repositories within the records database 126 such as HIE 142, VMR 144, EHR 140, etc. In an embodiment, the metadata layer repository 606 can be unified for all the records database 126 repositories.

The metadata validation system 404 may operate as a cloud-based enterprise-class, offering its services via one or more remote APIs that connect with CBRs 108 located at distributed locations. The metadata validation system 404 may be considered as a component of a PaaS, IaaS, SaaS, or other type of distributed architecture. In an embodiment, the metadata layer repository 606 may be integrated within a productivity application (e.g., word processor, spreadsheet, browser, etc.) that is configured to operate as the metadata validation appliance 602. In an embodiment, the metadata layer repository 606 may contain a single file associated with a single source document where the single file stores all annotations or other metadata for the source document. Such a file can be stored as a Binary Large Object (BLOB) or in any other form.

The metadata validation appliance 602 may link the metadata layer object 604 by storing an identifier to the source content. In an example, the identifier can direct a user or an administrator to the source document (e.g., a webpage) from which the content is imported. Examples of the source document identifier include a uniform resource locator (URL), a uniform resource identifier (URI), an IP address, a file name, an object reference, and other types of pointers. The identifier may also include a set of document coordinates that may point to the selected portion of the source document. The document coordinates can be a time index, a graphical coordinate, a paragraph number, a line number, a word number, a pair of document coordinate attributes, or document object model (DOM) element coordinate. When the source content is associated with one or more metadata layer object 604, the metadata validation appliance 602 may link the newly created metadata layer object instance to the one or more metadata layer objects 604 associated with the source content as parent metadata layer objects (e.g., by including a pointer to point to the one or more metadata layer objects 604). In some embodiments, the metadata validation appliance 602 may be configured to update the metadata layer objects 604 associated with the source content to include a link (e.g., a pointer) that points to the newly created metadata layer object instance as a child metadata layer object 604. The metadata validation appliance 602 may organize linkages and connections between various instances of the metadata layer objects 604 and source content pieces and also within multiple metadata layer objects 604. In an example, the metadata layer objects 604 may be updated in accordance with pre-defined internal and/or external taxonomies to facilitate organization and classification of the source documents that contain the health records originating from the content providers 102, 124, and 130 through the CBRs 108.

The metadata validation database 608 may store rights policies that specify different access levels and/or restrictions for different users and/or administrators who attempt to access the metadata layer object 604 based on different criteria. For example, the rights policies can be configured to specify different access rights/restrictions based on profile information of the administrator who tries to gain access to the metadata layer object 604, such as the role of the user within an organization who manages the records database 126 and/or the CBR 108. The rights policies may be configured to specify different access rights/restrictions for different administrators based on the different devices and networks that the administrators use to try to gain access to the metadata layer object 604. The authorization component 612 may process authorization and verification for allowing access to the metadata layer repository 606 based on the rights policies.

The server 614 may host various components and support systems for enabling technological infrastructure such as SaaS, HTTP, PaaS, IaaS etc. The server 614 may contain a special purpose processing circuitry and memory for processing various tasks.

The metadata validation system 404 may be communicatively connected with the network so as to allow leveraging from external taxonomies 704 (shown in FIG. 7) stored within external systems to improve machine learning-enabled structuring of the health records coming from the clinical data providers 104, 124, and networks 130 through the CBR 108.

Figure 7:
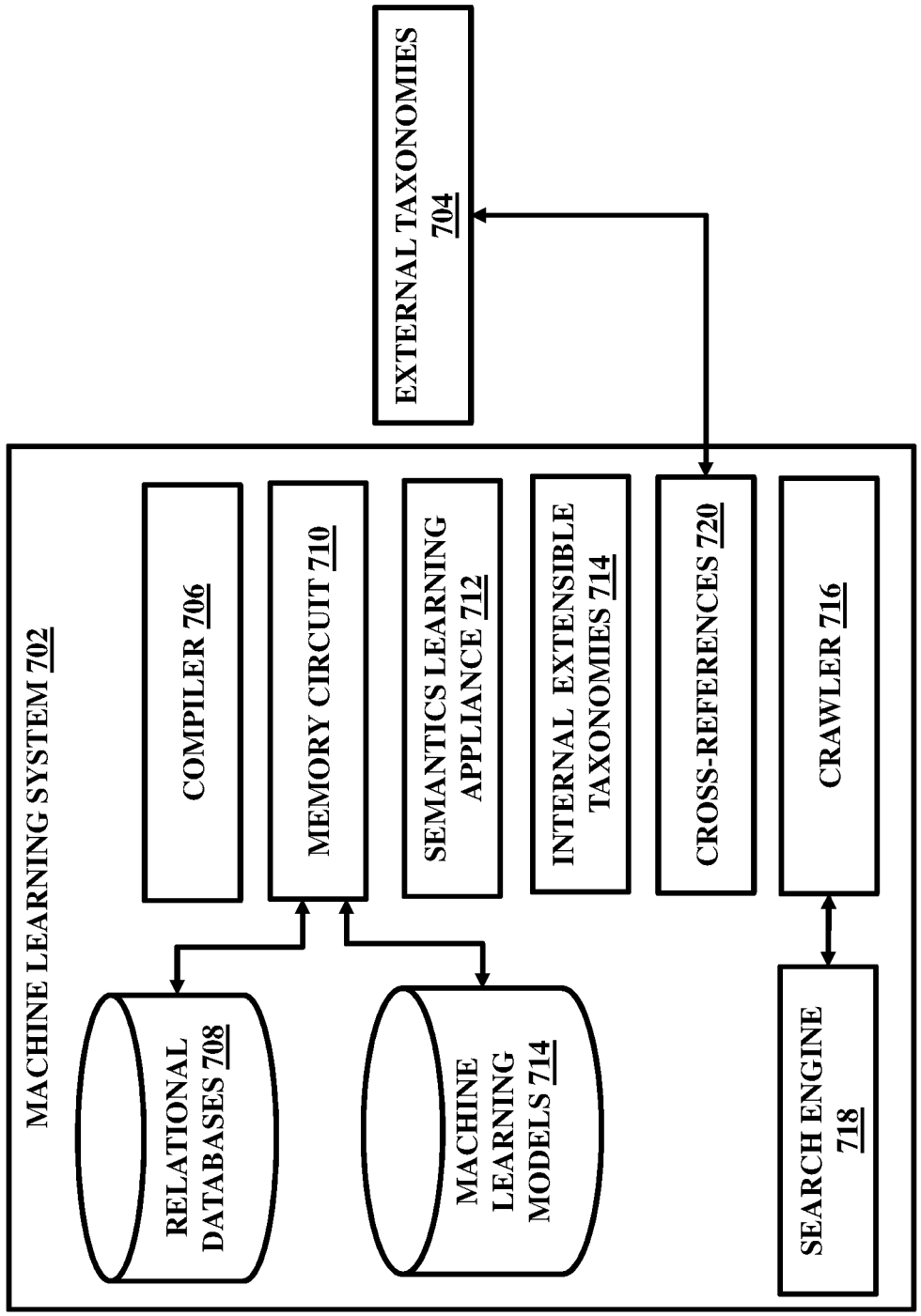
FIG. 7 illustrates a diagram of a machine learning system according to an embodiment herein.

FIG. 7 illustrates a machine learning system 702 configured within or coupled to the records database 126 and/or the CBR 108 and communicatively connected with or integrated within the data logging unit 148 for providing advanced machine learning functions in conjunction with data maintained by the master data validation system 402 and the metadata validation system 404 and learning overtime based on the stored master data and metadata generated perpetually within the enterprise or sources from the clinical data providers and networks 102, 124, 130 through the CBRs 108 located at gateways connecting between multiple providers 102, 124, 130 or at the records database 126 access point.

The machine learning system 702 may be configured to categorize the health records based on internal and external taxonomies, recognize patterns in the health records, structure the health records based on the taxonomies, metadata and master data, and machines and systems so trained.

The machine learning system 702 may include a compiler 706, relational databases 708, a memory circuit 710, and a semantics learning appliance 712. The compiler 706 may be configured to translate the model of relational databases 708 into structured components. The relational databases 708 may be of any type of relational databases configured to contain data of any type such as patient generated data, EHR, device generated data, data obtained from the content providers. In an example, the relational databases 708 may contain the data or a portion of the data that is stored in other repositories of the records database 126 such as the EHR. The relational databases 708 may be stored in the memory circuit 710 of the machine learning system 702.

The semantics learning appliance 712 may process rules and instructions stored in the memory circuit 710 for language and text mapping of multiple data elements. The semantics learning appliance 712 is configured to interpret machine learning models 714 that may be stored in the memory circuit 710 and to interpret data and its components by mapping element-by-element and field-by-field of an inflowing data from the content providers 102, 124, 130 and the data already generated and structured by the machine learning system 702 and stored in various data houses such as the records database 126 and its associated repositories, the metadata validation system 402 and the master data validation system 404. A 'field' herein in association with machine learning represents a header or an identifier of a column or row signifying content type in a particular column or row. An 'element' herein may represent actual information available under a 'field'. For example, a column may contain names of patients, the input 'name' may be defined as a 'field' while actual information about various individual names of the patients in the column may be termed as 'element' herein at least in conjunction with machine learning description. In examples, the machine learning models 714 may include such as one or more of a probablistic model, semantic model, language cue models, statistical models, extrapolation models, mathematical models, and analytical models.

The semantics learning appliance 712 may be configured to receive inputs from the metadata validation system 404 and the master data validation system 402. The semantics learning appliance 712 may interpret the inflowing health records coming from the content providers 102, 124, 130 using various probablistical, statistical, analytical, and interpretation models stored in the memory circuit 710. The semantics learning appliance 712 generates an output that provides an interpretation about what do various fields and elements in the inflowing data (also referred to as health records interchangeably) signify. The semantics learning appliance 712 may reference to the data stored in the metadata authentication and validation system 404, master data validation system 402 and the records database 126 and its associated repositories and then map the referenced data with the inflowing data to identify closest possible 'fields' and 'elements' of the referenced data in-context that may resemble the 'fields' and the 'elements' of the inflowing data. The closest resembling fields and elements of the inflowing data may be analysed for contextual evaluation to verify suitability of the resemblance in varying contexts and in particular context in consideration. The semantics learning appliance 712 may be configured to review other data elements and fields and words therein and compare with already structured corpus or dataset to identify the context and interpret meaning of the 'field' and the 'element' under consideration of the inflowing data. Once, a contextual relationship is associated and the 'field' and 'element' of the inflowing data is known precisely in context, the semantics learning appliance 712 may utilize internal extensible taxonomies 714 and the external taxonomies 704 to classify the interpreted 'field' and 'element' of the inflowing data. In a similar manner, various other fields and elements of the inflowing data may be interpreted by the machine learning system 702 to provide a structure to the inflowing data. Entire inflowing data is accordingly classified in taxonomical classes based on the internal extensible taxonomies 714 and the external taxonomies 704. In an embodiment, the semantics learning appliance 712 and various other components of the machine learning system 702 may be contained within or coupled to the records database 126 and/or the CBR 108 associated with the records database 126 and/or all the CBR 108.

The internal taxonomies 714 may be built over time based on available corpus in the records database 126 and various other associated repositories. The internal taxonomies 714 may be pre-defined by users or administrators or may be automatically generated through machine learning over time. In an embodiment, the internal extensible taxonomies 714 may be dynamic in the way that as more and more data flows into the records database 126 and associated repositories connected with the machine learning system 702 overtime, the machine learning system 702 may improve the internal extensible taxonomies 714 dynamically over time. The classified data, master data, and the metadata under various taxonomical classes may also be re-organized to reflect under updated taxonomical classes as and when an update happens in the internal extensible taxonomies 714. In an embodiment, the machine learning system 702 may utilize the external taxonomies 704 to classify the data, master data, and the metadata and also to improve the internal extensible taxonomies 714. The external taxonomies 704 may be associated with external systems not connected with the records database 126 directly. In an embodiment, the external systems may be various servers, databases, repositories, websites, information sources, etc which may be accessed by a crawler 716 to fetch the external taxonomies 704 or portions thereof into the machine learning system 702 automatically. The crawler 716 may include or be coupled to a search engine 718 to run periodic searches to find relevant taxonomies externally for contextual mapping of the health records and for ingestion into the machine learning system 702. The crawler 716 may use cross-references 720 maintained by the machine learning system 702 to access the external taxonomies 704 and may also update the cross-references 720 for any changes in the external taxonomies 704.

In an example, the machine learning system 702 may utilize inputs from the master data validation system 402 and the metadata validation system 404 to build the internal extensible taxonomies 714 so that each of the fields and elements within the metadata and the master data may be clustered by the machine learning system 702 around certain topics identified based on repeat behavior of words in the entire corpus of the master data and metadata to depict relative occurrences of the fields and elements defined by repeat words. The repeat behavior of fields and elements in the master data and the metadata may be used as an input to generate new taxonomical classes and refine the internal extensible taxonomies 714. For example, the machine learning system 702 may identify 'device compatibility' as one of the most repeat words around which the highest number of health records are clustered. The term 'device compatibility' may be noted as a topic for defining a set of relevant health records that may relate to 'device compatibility' and accordingly the machine learning system 702 may consider this term as a taxonomical class to refine the existing taxonomical classes in the internal extensible taxonomies 714 for classification of the health records. In an example, the master data and the metadata validation systems 402 and 404 may be communicatively connected with the machine learning systems 702. The semantics learning appliance 712 of the machine learning system 702 may apply contextual and linguistic techniques with the use of a language cue engine to identify clustering of health records around certain topics exhibiting repeat behavior and occurrences of certain words in the master data and the metadata.

The machine learning system 702 may utilize the internal extensible taxonomies 714 and the external taxonomies 704 to index the unstructured data and the structured data through automated mechanisms such as auto-indexing. In an example, the internal extensible taxonomies 714 may utilize controlled vocabulary to automatically apply the taxonomy classes or tags on the datasets (structured dataset and/or unstructured dataset) to classify the datasets in accordance with the predefined taxonomies (including the internal extensible taxonomies 714 and the external taxonomies 704). The machine learning system 702 may be trained by the administrators by adding a sample data and classifying the sample data manually or automatically in a controlled manner, in the beginning, in an embodiment. More sample data may be added in stages to train the machine learning system 702 better. As the machine learning system 702 recognizes the nature and patterns of data classification and tagging of the datasets in accordance with the taxonomies 704 and 714, the process of classification evolves over time so that with learnings from the past, the machine learning system 702 may perform automated structuring of the datasets. The machine learning system 702 may run periodic searches on the structured dataset to suggest additional terms for updating the internal extensible taxonomies 704.

In embodiments, the machine learning system 702 may be configured to maintain the internal extensible taxonomies 714 and the external taxonomies 704 so as to evolve and develop the internal extensible taxonomies 714.

The machine learning system 702 may create a new internal extensible taxonomy utilizing an existing internal extensible taxonomy and an existing external taxonomy by merging the existing internal extensible taxonomy with the existing external taxonomy based on a comparison of a category profile of the existing internal extensible taxonomy with a category profile of the existing external taxonomy. A category profile represents pattern of content terms as they occur in a tree-branch structure of a hierarchy associated with a taxonomy. The category profile may include digitally stored parent terms and digitally stored child terms and associated digital identifiers indicative of the respective digitally stored parent terms, digitally stored child terms and pointers indicating mutual connections among various child terms and parent terms in a hierarchical pattern. Therefore, by comparing category profiles, the machine learning systems 702 performs a search to identity matches between various content terms and patterns thereof in association with their placements along the tree-branch structure and determine which content terms from the category profile of the existing external taxonomy may resemble content terms from the category profile of the existing internal extensible taxonomy. Once matches are determined, the resembling content terms may be merged together so as to align according to the tree-branch structure and so that the hierarchy remains undisturbed. In a similar manner, the machine learning system 702 may perform category profile mapping for a plurality of the external taxonomies associated with multiple external systems in a way that each such external system may be crawled by the crawler and associated an identifier to associate an identity with a respective category profile of an associated external taxonomy of the plurality of external taxonomies.

In an embodiment, the machine learning system 702 may allow structuring of unstructured or semi-unstructured dataset in a faster approach by converting the unstructured dataset of the inflowing data from the content providers 102, 124, 130 to structured dataset utilizing the internal extensible taxonomies 714 and the external taxonomies 704 built into the master data validation system 402 and the metadata validation system 404.

In an example, the data logging unit 148 may be integrated with the machine learning system 702 or may be communicatively coupled to the machine learning system 702 so that the data logging unit 148 may be configured to apply advanced and improved natural language processing capabilities with the use of the master data and the metadata information and the available internal extensible taxonomies 714 and the externally pulled taxonomies 704 using the cross-references. In an example, the data logging unit 148 may be coupled to the master data validation system 402 and the metadata validation system 404 too. The data logging unit 148 may perform NLP functions so that the data logging unit 148 configured to process NLP tasks along with the machine learning system 702 to perform machine learning tasks may look for fields and elements in the inflowing unstructured dataset (also referred to as data interchangeably) and find them or similar fields and elements in the structured dataset already residing in the records database 126 and associated repositories and also identify the context in which those fields and names occur in the structured dataset. This allows the machine learning system 702 and the data logging unit 148 and the CBR 108 to recognize the unstructured or semi-structured inflowing dataset before storing it permanently in the records database 126 in a particular structured format. Thus, the machine learning system 702 and the data logging unit 148 may utilize NLP and machine learning capabilities to perform natural language processing and machine learning to recognize the unstructured dataset based on the past that is what has been structured in the records database 126 already in the past. Thus, the present invention not only utilizes the health records stored in the records database 126 but also the metadata and the master data contained in the master data validation system 402 and the metadata validation system 404 for enabling natural language processing-based and machine learning-based transformation of the unstructured and the semi-structured dataset to the structured dataset.

In an embodiment, the clinical data providers 104, 124, and networks 130 may be allowed to access the structured data stored in the records database 126 and associated repositories based on predefined rules and identity information about the clinical data providers 104 and 124. The records database 126 may allow the clinical data provider 104 and 124 if access to at least a portion of the structured data of the records database after verifying contextual information, device information, browser information, and network information associated the clinical data provider 104 and 124 by comparing it with pre-stored and pre-registered identity information about the clinical data provider 104 and 124. The identity information may be stored in a separate repository of the records database 126 and may include such as the device information, browser information, network information, and the contextual sensed information.

The device information may include information such as model, serial number, and other information of the computing device associated with the clinical data provider 104. The network information may indicate browser or network behavior. The contextual information may be indicative of sensed proximate environments such as weather, pollution, location, time etc.

Figure 8:
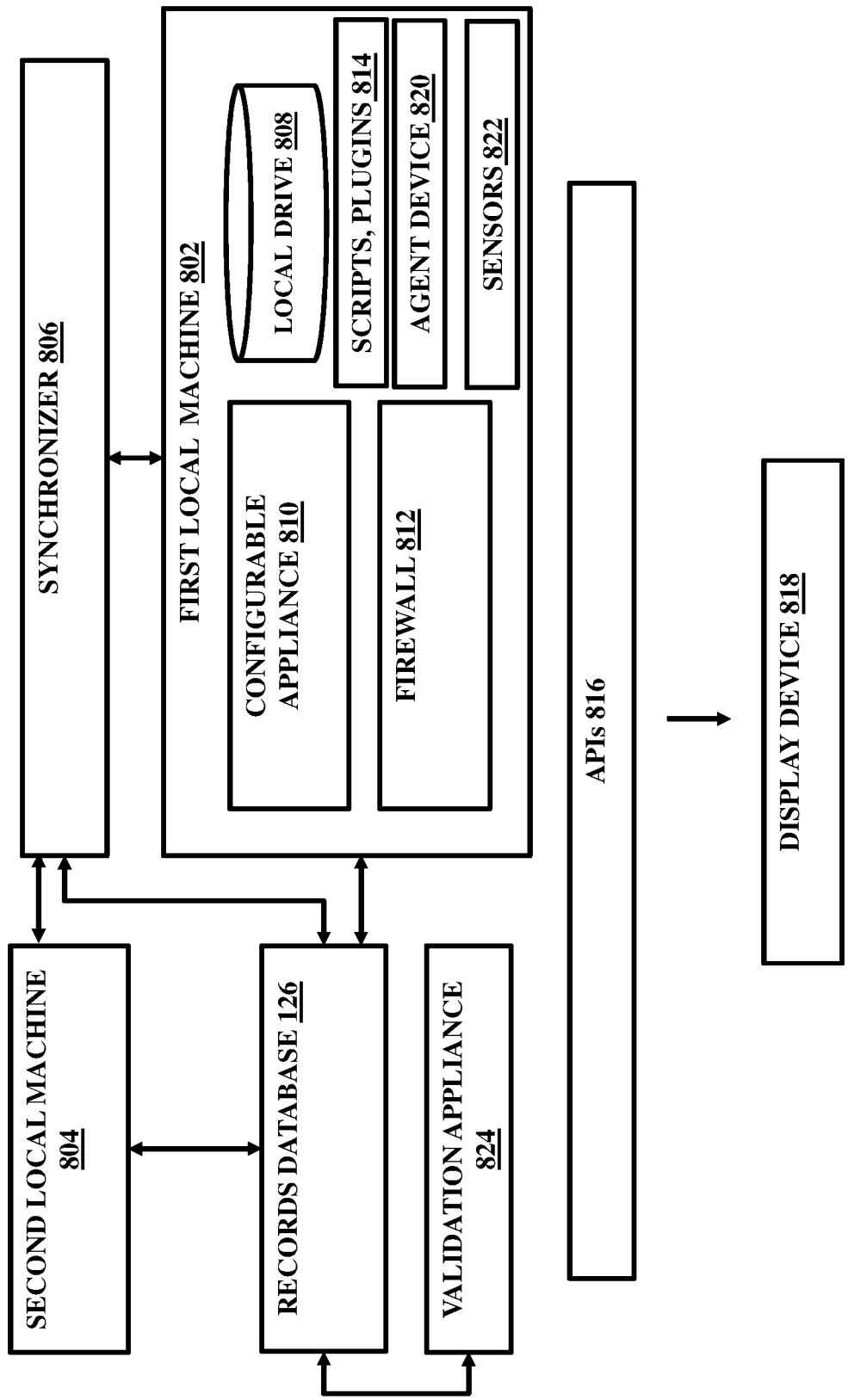
FIG. 8 illustrates a local hardware-based device associated with a clinical data provider computer to allow access, retrieval, and syndication of a portion of structured dataset locally according to an embodiment herein.

The accessed at least a portion of the structured data authorized to view and access by the clinical data provider such as the clinical data provider 104 may be shared with the clinical data provider 104 by synchronising the authorized accessed data to a local hardware-based device associated with the clinical data provider and located at a site of the clinical data provider 104. Such a local hardware-based device referred to as a first local machine 802 is shown in FIG. 8. In a similar manner, a second local machine 804 may be located at a site of the clinical data provider 124 to allow sharing of at least an authorized portion of the structured data stored in the records database 126. The data allowed to be accessed by the clinical data provider 104 and the data allowed to be accessed by the clinical data provider 124 may be different or may be same or may overlap based on access requests and based on identity information and access rights.

In accordance with the embodiments discussed herein, the first local machine 802 may be installed in a network zone of the clinical data provider 102 who may request to access the records database 126. The clinical data provider 104 may receive the requested data from the records database 125 upon verification and authorization directly from the cloud to the first local machine 802 installed within the network zone of the clinical data provider 104. The data can then be retrieved locally and accessed by the clinical data provider 104 in its network zone. A synchronizer 806 may dynamically update the data on a local drive 808 in accordance with evolution and updates in the structured data in the records database 126 based on access rights. The first local machine 802 can execute various tasks of sourcing, retrieving and downloading the accessed structured data at the local drive 808 with the use of a configurable appliance 810 of the first local machine 802 using the synchronizer 806. While the embodiment is discussed in conjunction with the first local machine 802 and associated components thereof, various embodiments can involve use of one or more additional similar or different local machines without limitations for other clinical data providers to access the structured data stored in the records database 126 after metadata and master data-based transformation as discussed above in the document. The information obtained from the cloud at the first local machine 802 may exist in the digital format as defined by the records database 126. In an embodiment, the data obtained from the cloud may be fragmented and the configurable appliance 810 may first organize the data before it is used by the users. The configurable appliance 810 may also allow manual process of data merging in accordance with an embodiment of the present invention. The configurable appliance 810 may be installed behind a firewall 812. The configurable appliance 810 may contain a set of scripts and plugins 814 and APIs 816 to allow presentation and display of the accessed data on a display device 818.

The first local machine 802 may include devices and appliances for sensing and gathering local and contextual information to transmit to the records database 126 for allowing the records database 126 to compare the transmitted information with the identity information. If the identity information matches the transmitted information, the clinical data provider 104 may be allowed to access the at least a portion of the structured data maintained by the records database 126.

The devices and appliances contained within the first local machine 802 for this purpose may include an agent device 820 to gather browser, device, and network information associated with the clinical data provider and transmit the gathered browser, device, and network information to the records database 126 for identity verification to authorize accessing of the at least a portion of the structured dataset stored in the records database 126. The first local machine 802 may further include a contextual sensor 822 fitted proximate the clinical data provider 104 for gathering contextual information about the respective clinical data provider 104 and transmitting the contextual information to the records database 126 for further verification. The records database 125 may be coupled to or may include a validation appliance 824 for identity verification to authorize accessing of the at least a portion of the structured dataset stored in the records database 126. The sensors 822 may of various types such as a location sensor, geospatial coordinate sensor, Global positioning system (GPS)-based device, weather sensor, internet of things-based devices (IoT devices), and the like to allow comparing by the validation appliance 824 such as real-time geo-spatial information with pre-registered location identity information maintained by the validation device, and the like. The Global Positioning System-based (GPS-based) device may be configured to sense geo-spatial information indicative of location coordinates and transmit the sensed geo-spatial information to the blockchain configured records database 126 for verification of the identity of the associated clinical provider computer. The validation appliance 824 may store the predefined device information, network information, location information (geo-spatial information), contextual information, and the like and is configured to compare this predefined information with real time information coming in from the agent device 820 and the sensors 822 to allow access to the structured dataset at least in part stored in the records database 126. Similar local machines may be associated with other clinical data providers such as 124. Such local machines may be housed within a physical, tangible material frame made of metal, non-metal or plastic material capable of being fitted and installed at a physical location.

Figure 9:
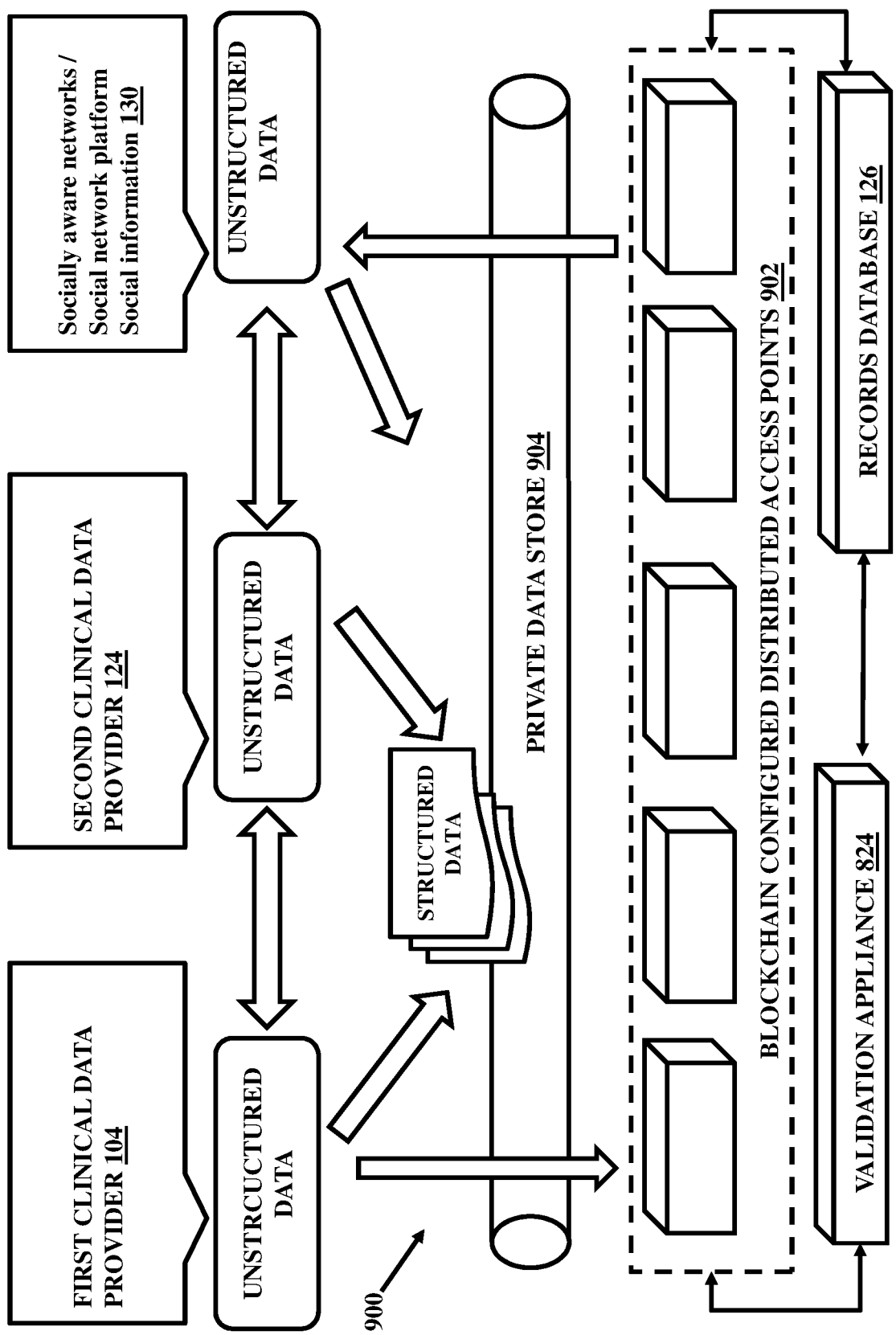
FIG. 9 illustrates a blockchain configured ecosystem according to an embodiment herein.
Figure 10:
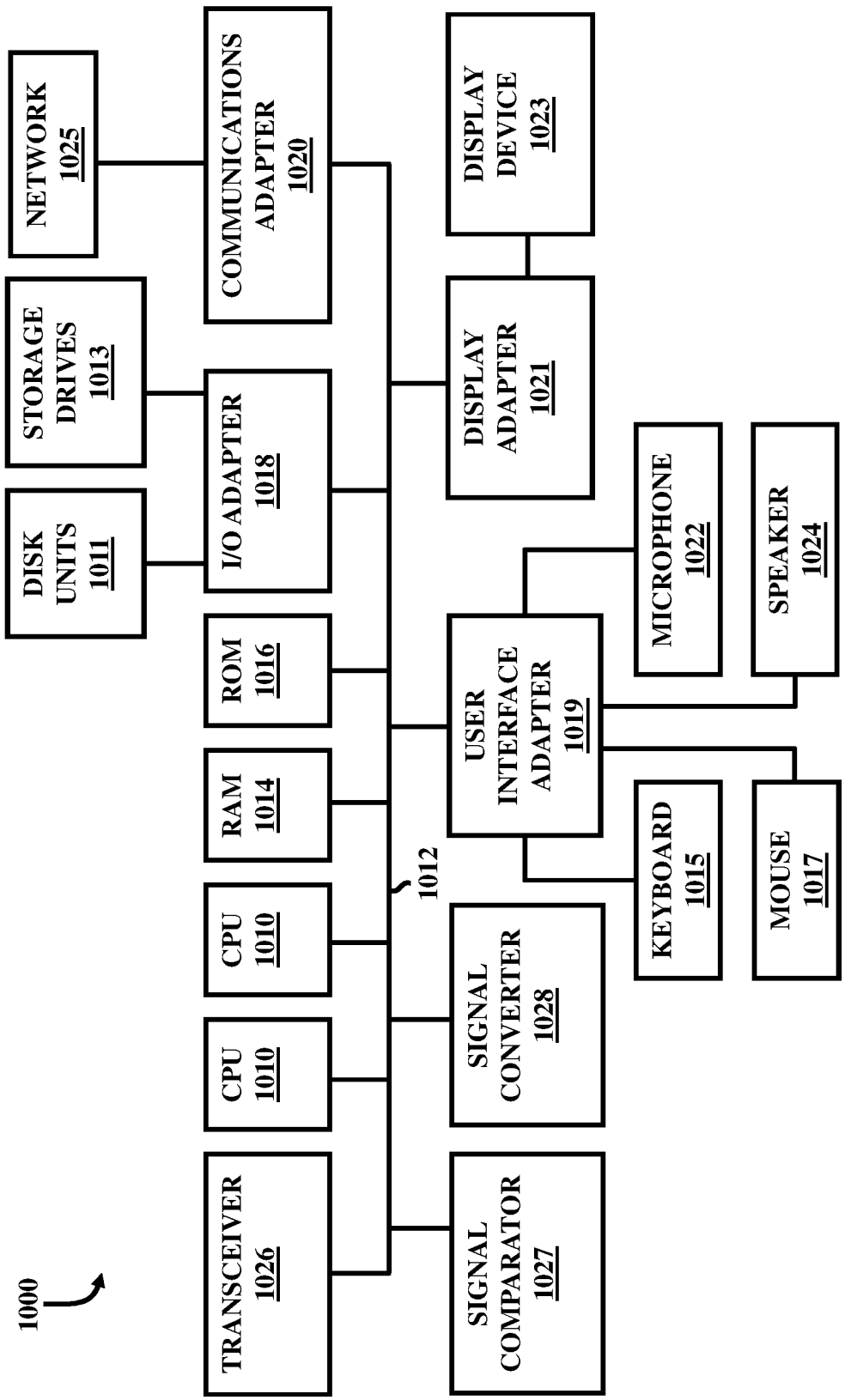
FIG. 10 is a schematic diagram illustrating a computer system according to an embodiment herein.

FIG. 9 illustrates an exemplary blockchain configured ecosystem 900 for facilitating transformation of the unstructured and semi-structured data into the structured data using various techniques and appliances and machines as discusses earlier in conjunction with various figures.

The blockchain configured records database 126 may provide a private view to the clinical data providers 104 and 124 who may want to access the structured data based on access right referred to as private data store 904 so that each clinical data provider 104 and 124 can privately access certain documents based on various policies and based on verification by the validation device 824. Each of the clinical data providers 104 and 124 may access the structured data through the dedicated private store 904 available through the plurality of distributed blockchain configured access points 902 which may be enabled in the form of distributed blocks by the records database 126 as shown in FIG. 9, with each block providing a facility to access the blockchain configured structured data by the clinical data providers 104 and 124 at the same time based on defined and granted access rights.

The private data store 904 may provide a virtual storage to facilitate interaction, information exchange, reviewing, and presentation of the structured data according to granted access for clinical data providers 104 and 124. For example, the private data store 904 may allow a virtual storage and presentation of only limited documents or portions of the structured data for access by the clinical data providers 104 and 124 in accordance with permissions granted to the clinical data providers 104 and 124. The private data store 904 may be configured to auto-hash review interactions at any required interval. This compartmentalization of the documents ensures that the documents are secured and private as per access rights authorized to the clinical data providers 104 and 124. The data presented on the private data store 904 of the blockchain serves as a secure way to ensure that the private data store 904 is in sync with any permissioned access.

In an embodiment, the blockchain configured digital ecosystem 900 may provide a federated blockchain consisting of several entities/participants and associated computers and devices and sensors that jointly access the structured data through a trusted, secured and distributed network of the blockchain configured access points 902. Federations can be organized by systems of care such as identified by geography, e.g. community or state. The clinical data providers 104 and 124 may be assumed to stay within these systems of care that cross organizations. In an example, the federated blockchain may be applied on top of an existing health information exchange community as a way to further reduce costs and help the community reach financial sustainability.

In accordance with an embodiment, the clinical data providers 104 and 124 can access the structured data based on authorization and access rights granted which may dynamically be updated in accordance with the contextual information received from the clinical data providers 104 and 124 and associated devices and sensors. The blockchain configured validation appliance 824 may be configured to validate identity of the clinical data providers 104 and 124 accessing the structured data to establish a trusted information access process. The blockchain configured identity validation appliance 824 may utilize a variety of identity validation algorithms and schemes such as but not limited to facial expressions, geographical coordinates, geo-tags, gestures, muscle activity, and the like. In accordance with a specific type of validation scheme utilized by the blockchain validation device 824, a validation scheme-based device may be utilized.

In an example, the embodiments herein can provide a computer program product configured to include a pre-configured set of instructions, which when performed, can result in actions as stated in conjunction with the method(s) described above. In an example, the pre-configured set of instructions can be stored on a tangible non-transitory computer readable medium. In an example, the tangible non-transitory computer readable medium can be configured to include the set of instructions, which when performed by a device, can cause the device to perform acts similar to the ones described here.

The embodiments herein may comprise a computer program product configured to include a pre-configured set of instructions, which when performed, can result in actions as stated in conjunction with the methods described above. In an example, the pre-configured set of instructions can be stored on a tangible non-transitory computer readable medium or a program storage device. In an example, the tangible non-transitory computer readable medium can be configured to include the set of instructions, which when performed by a device, can cause the device to perform acts similar to the ones described here. Embodiments herein may also include tangible and/or non-transitory computer-readable storage media for carrying or having computer executable instructions or data structures stored thereon.

Generally, program modules include routines, programs, components, data structures, objects, and the functions inherent in the design of special-purpose processors, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can include both hardware and software elements. The embodiments that are implemented in software include but are not limited to, firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments herein is depicted in FIG. 8, with reference to FIGS. 1 through 7. This schematic drawing illustrates a hardware configuration of an information handling/computer system 1000 in accordance with an exemplary embodiment herein. The system 1000 comprises at least one processor or central processing unit (CPU) 1010. The CPUs 1010 are interconnected via system bus 1012 to various devices such as a random access memory (RAM) 1014, read-only memory (ROM) 1016, and an input/output (I/O) adapter 1018. The I/O adapter 1018 can connect to peripheral devices, such as disk units 1011 and storage drives 1013, or other program storage devices that are readable by the system. The system 1000 can read the inventive instructions on the program storage devices and follow these instructions to execute the methodology of the embodiments herein. The system 1000 further includes a user interface adapter 1019 that connects a keyboard 1015, mouse 1017, speaker 1024, microphone 1022, and/or other user interface devices such as a touch screen device (not shown) to the bus 1012 to gather user input. Additionally, a communication adapter 1020 connects the bus 1012 to a data processing network 1025, and a display adapter 1021 connects the bus 1012 to a display device 1023, which provides a GUI (e.g., a gadget) in accordance with the embodiments herein, or which may be embodied as an output device such as a monitor, printer, or transmitter, for example. Further, a transceiver 1026, a signal comparator 1027, and a signal converter 1028 may be connected with the bus 1012 for processing, transmission, receipt, comparison, and conversion of electric or electronic signals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A blockchain configured geographically distributed architecture-based system connected over a communication network for transforming an unstructured or semi-structured dataset to a structured computerized dataset fora blockchain configured records database communicatively coupled to a plurality of blockchain configured content based routers receiving said unstructured or semi-structured dataset from a plurality of data provider computers in a blockchain-enabled network, said system comprising:
   a first proxy database, stored on a first tangible non-transitory computer readable medium and comprising a first special purpose processing device implemented on a first integrated circuit chip, configured to:

create a backup of data associated with a first data provider computer, wherein said data associated with said first data provider computer is in a first digital format; and communicate with said first data provider computer for backing up said data associated with said first data provider computer, through a first proxy object, wherein said first proxy object comprises one or more references to said first proxy database to establish a connection between said first data provider computer and said first proxy database through one or more database drivers;

a blockchain configured first content based router of said plurality of blockchain configured content based routers, comprising a second special purpose processing device implemented on a second integrated circuit chip, configured to:

collect said data associated with said first data provider computer from said first proxy database; and convert said data associated with said first data provider computer to said structured computerized dataset in accordance with a standardized digital format of datasets associated with said blockchain configured records database, wherein said blockchain configured first content based router is physically located at a gateway associated with said first data provider computer providing a first digital data access point of said distributed blockchain configured records database to said first data provider computer;

said blockchain configured records database stored on a third tangible non-transitory computer readable medium and comprising a third special purpose processing device implemented on a third integrated circuit chip to store and index said structured computerized dataset in said standardized digital format of datasets associated with said blockchain configured records database, and providing a plurality of distributed digital data access points including said first digital data access point communicatively connecting with said first data provider computer through said first digital data access point of said plurality of distributed digital data access points;

a master data validation system communicatively and operatively coupled to said blockchain configured first content based router and said blockchain configured records database and including a master data repository to store master data instances in said standardized digital format of datasets associated with said blockchain configured records database on a tangible non-transitory memory device; and a metadata validation system that is different and separately located from said master data validation system and communicatively and operatively coupled to said blockchain configured first content based router, and said master data validation system, and configured to store linkable metadata layer objects in a metadata layer repository and digitally link said metadata layer objects by storing an identifier to a source content residing in said blockchain configured records database, wherein said blockchain configured first content based router is connected to a machine learning system contained within said blockchain configured records database, said machine learning system comprising:

internal extensible taxonomies built in a computerized format based on said structured computerized dataset in said blockchain configured records database, said internal extensible taxonomies are defined through a computerized category profile wherein said computerized category profile includes digitally stored parent terms and digitally stored child terms and associated digital identifiers indicative of said respective digitally stored parent terms, digitally stored child terms and pointers indicating mutual connections in a hierarchical pattern, wherein said internal extensible taxonomies are automatically generated through machine learning over a period of time, and vs/herein said machine learning system receives inputs from said master data validation system and said metadata validation system to build said internal extensible taxonomies;

external taxonomies pulled from external systems not connected with said blockchain configured records database directly and crawled by accessing said external systems with the use of a search engine-enabled crawler to merge with said internal extensible taxonomies digitally by mapping comparable terms in said external taxonomies with said category profile of said internal extensible taxonomies;

a memory circuit to store said internal extensible taxonomies and said external taxonomies that are digitally merged with said internal extensible taxonomies; and a semantics learning appliance comprising a fourth special purpose processing device implemented on a fourth integrated circuit chip configured to perform mapping of said inflowing unstructured or semi-structured dataset with said structured computerized dataset already stored in said blockchain configured records database and said master data and said metadata;

wherein a dedicated first local machine housed in a material frame is operatively and communicatively coupled to said first data provider computer and installed physically behind a firewall and communicatively connected with said remotely located blockchain configured records database to transmit said structured computerized dataset at least in part from said blockchain configured records database to said first data provider computer through a digital transmission channel based on access rights and upon identity verification of said first local machine by said blockchain configured records database, and wherein said first local machine comprises:

a first agent device configured to gather browser, device, and network information associated with said data provider computer and transmit said gathered browser, device, and network information to said blockchain configured records database for identity verification to authorize accessing of at least a portion of said structured computerized dataset stored in said blockchain configured records database, and a first contextual sensor fitted proximate to said first data provider computer physically for gathering contextual information about said first data provider computer and transmitting said contextual information to said blockchain configured records database for further identity verification to authorize accessing of said at least a portion of said structured computerized dataset stored in said blockchain configured records database, wherein said first contextual sensor comprises a Global Positioning System-based (GPS-based) device configured to sense geo-spatial information indicative of location coordinates and transmit said sensed geo-spatial information to said blockchain configured records database for verification of identity, of said first data provider computer.

2. The system of claim 1, wherein said one or more database drivers comprising a Java Database Connectivity and Open Database Connectivity (JDBC-ODBC) Driver.

3. The system of claim 1, wherein said first blockchain configured content based router comprises an HL7 content based router that collects said data from said first proxy database.

4. The system of claim 1, wherein said master data validation system further comprising:
- a master data validation interface configured as a role-based graphical user interface (GUI) to allow user access to said master data;
- a parameter store module to provide an adaptive extensible framework for unified master data across entire multiple data repositories associated with said blockchain configured records database and control information that specifies behavior of master data validation processes and data representation using a set of pre-defined rules and guidelines;
- an abstraction layer configured as an application programming interface (API) that enables other systems to access and manipulate said master data in a defined way; and
- a data integration appliance including specialized hardware and software components for computerized data extraction, transformation and ingestion into said master data repository.

5. The system of claim 1, wherein said metadata validation system further comprising:
- a metadata layer repository configured to store linkable metadata layer objects;
- a metadata authentication and validation device to store rights policies that specify different access levels and restrictions for different users who attempt to access said metadata layer object; and
- a server to host components and support systems for enabling technological infrastructure of said metadata validation system.

6. The system of claim 1, wherein said machine learning system further comprises machine learning models stored within said memory circuit for enabling interpretation of said unstructured and semi-structured dataset and its components by said mapping by said semantics learning appliance.

7. The system of claim 1, wherein said machine learning models comprise one or more of a probabilistic model, semantic model, language cue models, statistical models, extrapolation models, mathematical models, and analytical models.

8. The system of claim 1, wherein said search engine-enabled crawler is configured to fetch said external taxonomies or portions thereof into said machine learning system automatically, said search engine-enabled crawler including or be coupled to a search engine to run periodic searches to find relevant taxonomies externally for computerized contextual mapping, computerized categorizing, and computerized transformation of said unstructured or semi-structured dataset into said structured computerized dataset.

9. The system of claim 1, wherein said master data validation system is configured to create a computerized unified view of enterprise data specifying each instance of a business element through digital identifiers.

10. The system of claim 1, wherein said semantics learning appliance is further configured to:
- interpret machine learning models stored in said memory circuit;
- map, element-by-element and field-by-field, said inflowing unstructured or semi-structured dataset from said plurality of data provider computers with said structured computerized dataset already generated and structured by said machine learning system and stored in said blockchain configured records database to identify closest possible 'fields' and 'elements' from said structured computerized dataset stored in said blockchain configured records database that resemble said 'fields' and said 'elements' of said inflowing unstructured and semi-structured dataset;
- reference to metadata and master data stored in said metadata validation system and said master data validation system; and
- map said referenced data within said master data validation system and said metadata validation system with said inflowing unstructured or semi-structured dataset to identify closest possible 'fields' and 'elements' of said referenced data in-context that resemble said 'fields' and said 'elements' of said inflowing data.

11. The system of claim 1, wherein said blockchain configured records database comprising a validation appliance configured to compare said browser, device, network, and contextual information transmitted by said first sensor and said first agent device with pre-stored identity information of said first data provider computer to verify said identity of said first data provider computer and allow access to said at least a portion of said structured computerized dataset upon verification through said first blockchain configured access point connected with said blockchain configured records database in a distributed facility.

12. The system of claim 1, further comprising:
- a second proxy database, stored on a second tangible non-transitory computer readable medium and comprising a fifth special purpose processing device implemented on a fifth integrated circuit chip, configured to:
  - create a backup of data associated with a second data provider computer, wherein said data associated with said second data provider computer is in a second digital format which is different from said first digital format; and
  - communicate with said second data provider computer for backing up said data associated with said second data provider computer, through a second proxy object, wherein said second proxy object comprises a second reference to said second proxy database to establish a second connection between said second data provider computer and said second proxy database through a second database driver; and
- a blockchain configured second content based router comprising a fourth sixth special purpose processing device implemented on a sixth integrated circuit chip, configured to:
  - collect said data associated with said second data provider computer from said second proxy database; and
  - convert said data associated with said second data provider computer to said structured computerized dataset in accordance with said standardized digital format of datasets associated with said blockchain configured records database, wherein said blockchain configured second content based router is physically located at a gateway associated with said second data provider computer providing a second digital access point of said distributed blockchain configured records database to said second data provider computer.

13. The system of claim 1, wherein said semantics learning appliance is further configured to:
- process rules and instructions stored in said memory circuit for language and text mapping of said inflowing unstructured or semi-structured dataset at digital fields and digital elements level, wherein said digital fields represent a digitally stored data header identifier in a computer-controlled data structure and said digital elements represent a plurality of digital data objects within said respective digital fields including pointers that connect said digital data objects to said respective digital fields;
- transform said inflowing unstructured or semi-structured dataset to said fully structured computerized dataset based on said mapping of said fields and said elements of said inflowing unstructured or semi-structured dataset with said computerized structured dataset already stored in said blockchain configured records database and said master data and said metadata; and
- utilize said internal extensible taxonomies and said external taxonomies to classify said inflowing unstructured or semi-structured dataset and store said inflowing unstructured or semi-structured dataset in relevant taxonomy classes in said blockchain configured records database after said transformation to said structured computerized dataset.

\* \* \* \* \*